US007155306B2

(12) United States Patent
Haitin et al.

(10) Patent No.: US 7,155,306 B2
(45) Date of Patent: Dec. 26, 2006

(54) MEDICATION ADMINISTRATION SYSTEM

(75) Inventors: David Haitin, Tel Aviv (IL); Gilead Asseo, Kfar Maas (IL); Batami Sadan, Tel Aviv (IL)

(73) Assignee: MDG Medical, Inc., Beachwood, OH (US)

( * ) Notice: Subject to any disclaimer, the term of this patent is extended or adjusted under 35 U.S.C. 154(b) by 215 days.

(21) Appl. No.: 10/318,139

(22) Filed: Dec. 12, 2002

(65) Prior Publication Data

US 2003/0120384 A1    Jun. 26, 2003

Related U.S. Application Data

(63) Continuation-in-part of application No. 09/706,872, filed on Nov. 7, 2000, now Pat. No. 6,636,780, and a continuation-in-part of application No. PCT/IL01/01030, filed on Nov. 6, 2001.

(51) Int. Cl.
G07F 17/00    (2006.01)
(52) U.S. Cl. ..................................... 700/242
(58) Field of Classification Search ................ 700/242, 700/241
See application file for complete search history.

(56) References Cited

U.S. PATENT DOCUMENTS

| | | | |
|---|---|---|---|
| 4,783,740 A * | 11/1988 | Ishizawa et al. ............... 705/28 |
| 4,785,969 A | 11/1988 | McLaughlin | |
| 4,847,764 A | 7/1989 | Halvorson | |
| 4,857,713 A | 8/1989 | Brown | |
| 4,857,716 A | 8/1989 | Gombrich et al. | |
| 5,014,875 A | 5/1991 | McLaughlin et al. | |
| 5,401,059 A | 3/1995 | Ferrario | |
| 5,460,294 A | 10/1995 | Williams | |
| 5,536,084 A | 7/1996 | Curtis et al. | |
| 5,564,803 A | 10/1996 | McDonald et al. | |
| 5,572,873 A * | 11/1996 | Lavigne et al. ............... 62/3.62 |
| 5,646,912 A * | 7/1997 | Cousin ........................ 368/10 |

(Continued)

OTHER PUBLICATIONS

Goring, J., "Automation Has Already Changed The Way We Work—And More Is Yet To Come," *Brave New World* (1999).

(Continued)

*Primary Examiner*—Patrick Mackey
*Assistant Examiner*—Michael E Butler
(74) *Attorney, Agent, or Firm*—Dilworth Paxson LLP; John W. Goldschmidt, Jr.

(57) ABSTRACT

The present invention comprises a system and method for administering medications to a plurality of patients in a medication institution. A preferred system comprises a workflow program for generating a scheduler, wherein the scheduler coordinates the administration of medications to the patients, a medicine cabinet, responsive to said scheduler, for storing medications and dispensing the medications to an authorized user for administration to the patients, the workflow program providing the cabinet with patient specific information relating to said dispensation of the medications including a physician order for each patient, and a medicine cart, coupled to the medicine cabinet, for instructing said authorized user in the administration of said medication to each of said patients. The cart comprises a plurality of patient specific cart drawers for storing the medication to be administered to each patient, wherein each cart drawer remains unidentified as patient specific until the medication cart receives said patient specific information, and a cart processor, wherein the cart drawers are filled with medicine from the medicine cabinet for each patient associated with each patient specific cart drawer in accordance with the respective physician order for each patient.

11 Claims, 17 Drawing Sheets

U.S. PATENT DOCUMENTS

| | | | |
|---|---|---|---|
| 5,673,983 | A | 10/1997 | Carlson et al. |
| RE35,743 | E | 3/1998 | Pearson |
| 5,745,366 | A | 4/1998 | Higham et al. |
| 5,758,095 | A | 5/1998 | Albaum et al. |
| 5,842,976 | A | 12/1998 | Williamson |
| 5,845,255 | A | 12/1998 | Mayaud |
| 5,845,264 | A | 12/1998 | Nellhaus |
| 5,883,806 | A | 3/1999 | Meador et al. |
| 5,905,653 | A | 5/1999 | Higham et al. |
| 5,912,818 | A | 6/1999 | McGrady et al. |
| 5,927,540 | A | 7/1999 | Godlewski |
| 5,945,651 | A | 8/1999 | Chorosinski et al. |
| 6,003,006 | A | 12/1999 | Colella et al. |
| 6,011,999 | A | 1/2000 | Holmes |
| 6,021,392 | A | 2/2000 | Lester et al. |
| 6,032,155 | A | 2/2000 | De la Huerga |
| 6,068,156 | A | 5/2000 | Liff et al. |
| 6,112,502 | A | 9/2000 | Frederick et al. |
| 6,116,461 | A * | 9/2000 | Broadfield et al. ........... 221/98 |
| 6,151,536 | A | 11/2000 | Arnold et al. |
| 6,152,364 | A | 11/2000 | Schoonen et al. |
| 6,170,929 | B1 | 1/2001 | Wilson et al. |
| 6,175,779 | B1 * | 1/2001 | Barrett ....................... 700/242 |
| 6,189,727 | B1 | 2/2001 | Shoenfeld |
| 6,272,394 | B1 | 8/2001 | Lipps |
| 6,272,481 | B1 | 8/2001 | Lawrence et al. |
| 6,339,732 | B1 | 1/2002 | Phoon et al. |
| 6,347,329 | B1 | 2/2002 | Evans |
| 6,352,200 | B1 | 3/2002 | Schoonen et al. |
| 6,385,505 | B1 | 5/2002 | Lipps |
| 6,421,650 | B1 | 7/2002 | Goetz et al. |
| 6,604,019 | B1 * | 8/2003 | Ahlin et al. ................. 700/231 |
| 6,636,780 | B1 * | 10/2003 | Haitin et al. ................ 700/236 |
| 6,769,568 | B1 | 8/2004 | Bonini et al. |
| 6,985,797 | B1 * | 1/2006 | Spano et al. ................. 700/237 |
| 7,006,894 | B1 * | 2/2006 | de la Huerga ............. 700/244 |
| 2001/0002448 | A1 | 5/2001 | Wilson et al. |
| 2001/0044731 | A1 | 11/2001 | Coffman, et al. |
| 2002/0027507 | A1 | 3/2002 | Yarin et al. |
| 2002/0032582 | A1 | 3/2002 | Feeney, Jr. et al. |
| 2002/0035484 | A1 | 3/2002 | McCormick |
| 2002/0070226 | A1 | 6/2002 | Liff et al. |
| 2002/0091546 | A1 | 7/2002 | Christakis et al. |
| 2002/0095424 | A1 | 7/2002 | Chung |

OTHER PUBLICATIONS

Larson, J., "Bar Code Technology: Raising the 'Bar' on Medication Error Reduction," *NurseZone.com* 1-3 (2002).
Sandrick, K., "Automating the Dispension of Medication," *Health Mgmt Tech*, 26(1) (1998).
Shaw, A., "Wireless Systems Improve Point-Of-Care Computing For Doctors and Nurses," *Can. Health. Tech.* (1999).
Richards, F., "Pill Delivery Goes Robotic," *Med. Equip. Designer* (2000).
Kremsdorf, R., "Medication Safety Tools 2002 Evaluation of Vendor Offerings for Computerized Physician Order Entry and Medication Administration," *Five Rights Consulting, Inc.* 1-89 (2002).
Wise, L.C., et al., "Cost-Benefit Analysis of an Automated Medication System," *Nurs. Economics* 4(14):224 (1996).
"White Paper on Automation in Pharmacy," Amer. Society of Consultant Pharmacists, http://www.ascp.com (1998).
"Right Patient, Right Medication, Right Time," http://www.abs.ca (2002).
"Wireless Solutions," Eclipsys The Outcomes Company www:eclipsys.com (2002).
"Dispensing, With Robots," Business Line, http://www.blonnet.com (2001).
"AUTROS Unveils New Mobile Medication Car—AUTROS Healthcare Solutions announces the arrival of the 'AUTROS Grand Med Depot'", AUTROS Healthcare Solutions http://www.autros.com (2000).

* cited by examiner

MEDICATION ADMINISTRATION SYSTEM

CROSS REFERENCE TO RELATED APPLICATIONS

This application is a continuation in part of U.S. patent application Ser. No. 09/706,872 filed Nov. 7, 2000 now U.S. Pat. No. 6,636,780; and PCT Patent Application No. PCT/IL01/01030 filed Nov. 6, 2001, which are each herein incorporated in its entirety.

BACKGROUND OF THE INVENTION

The present invention relates to medication administration systems. More specifically, the present invention relates to medication administration systems in a medical facility.

Automated medication dispensing systems have been in use for many years. The initial purpose of such systems was to reduce the high rates of medication errors associated with manual distribution and the high cost of maintaining a large amount of inventory. The literature indicates that medication errors occur in the following areas: 13% at prescribing, 42% at administering, 27% at documentation, 17% at dispensing and 1% at monitoring (Summary of Information Submitted to MEDMARX™ in the Year 2000). The current automated systems present more sophisticated advantages, including: lower costs associated with pharmaceutical distribution, reduction of personnel, inventory control, substance control, automated documentation, further reduction of errors, and relieving professional pharmacists and nursing personnel of many tasks.

There are two types of methods and currently two ways of dispensing medications employed in medical facilities: centralized systems, and decentralized systems.

The centralized systems are based on the transfer of the physician's orders/prescription to the central pharmacy of the medical facility. These systems facilitate the transfer of orders/prescriptions to the central pharmacy after being reviewed by personnel in the ward/floor, whereupon the orders/prescriptions are reviewed, authorized and filled by a pharmacist, sent as a unit dose to the ward, where every patient has a personal container, usually at a central location, that contains all his medicine for the next 24 hours, and then dispensed to the appropriate patient according to each individual hospital's routines. Centralized systems are used primarily in the U.S.A. They are costly and very inefficient, mainly because of the use of a large trained staff.

Decentralized systems arc based on ward stocks managed by trained nursing personnel in conjunction with pharmacists from the hospital pharmacy. The dispensing procedure traditionally proceeds as follows:

The nurse receives from the physician the prescription/s stating the medication, time of delivery, and route (p.o., I.V., etc.).

At the appropriate time, the nurse retrieves the appropriate medication/s for the patients according to a list of orders, places the medications into a receptacle, usually with an attachment that indicates the patient's name, places the receptacles on a tray, and then dispenses the receptacles to the patients in the ward.

The foregoing traditional method is subject to a number of disadvantages including: (1) possible confusion between patient files; (2) errors in brand or dosage when retrieving medications from the medicine cabinet; (3) errors in identifying individual patients; (4) errors in receptacle identification; (5) a demand on much of the nurse's time; (6) possibility of mistakes in inventory record keeping and pharmacy ordering; and (7) very low degree of control, even though expensive and/or narcotic drugs are involved.

A report from the Institute of Medicine (IOM) of the National Academies released in November 1999 in the U.S.A. calls on Congress to create a national patient safety center to develop new tools and systems, the reason being alarming figures regarding the human cost of medical errors. Deaths from medical errors are estimated, according to different studies, to be between 44,000 to 98,000 people in the U.S. hospitals each year, which is more than those from highway accidents, breast cancer or AIDS. The report states that illegible handwriting, and the non-coordinated treatment of patients by several practitioners who do not have complete information about the medicines prescribed and the patient's illnesses, are part of the basic flaws in the way the health system is presently organized. William Richardson, chairman of the committee, is quoted as saying "It may be part of human nature to err, but it is also part of human nature to create solutions, find better alternatives, and meet the challenges ahead."

Medication management devices generally fall under three categories: (a) automated devices in the central pharmacy area; (b) automated devices in the patient care unit; and (c) point-of-care information systems.

The primary goal of using centrally-located devices is to replace or improve the current manual process for filling unit dose containers. These devices offer the advantage of a lower, single, centralized inventory: Disadvantages of such devices include large size, high cost, and reliance on efficient delivery systems from the central pharmacy.

Many systems have been proposed and are described in the literature for minimizing or eliminating the above-described disadvantages of the existing systems. Examples of such recent developments are described in U.S. Pat. Nos. 6,032,155; 6,021,392; 5,912,818; 5,314,243; 5,564,803; 6,003,006; 6,068,156; 5,842,976; 5,797,515; 5,014,875; 5,460,294; and 5,713,485.

However, prior to the present invention there has been a very pressing need to provide a flexible medication dispensing system which utilizes both the centralized and decentralized methods of dispensing medication, and meets at least the following goals: (1) provides secure and reliable medication dispensing; (2) permits more efficient workflow; (3) allows for the collection of vital signs (e.g., temperature, pulse rate and blood pressure); (4) maximizes automation and employs computerized paperless operation; (5) automates management of drug inventory in each department; (6) protects against "drug abuse" by medical and paramedical personnel; and (7) offers special protection for narcotic drugs.

SUMMARY OF THE INVENTION

An object of the present invention is to provide a medication dispensing system, and also a medicine cabinet structure and enabling attaining one or more of the foregoing goals.

Accordingly, the present invention comprises a system and method for administering medications to a plurality of patients in a medication institution. A preferred system comprises a workflow program for generating a scheduler, wherein the scheduler coordinates the administration of medications to the patients, a medicine cabinet, responsive to said scheduler, for storing medications and dispensing the medications to an authorized user for administration to the patients, the workflow program providing the cabinet with patient specific information relating to said dispensation of the medications including a physician order for each patient, and a medicine cart, coupled to the medicine cabinet, for instructing said authorized user in the administration of said medication to each of said patients. The cart comprises a plurality of patient specific cart drawers for storing the medication to be administered to each patient, wherein each cart drawer remains unidentified as patient specific until the medication cart receives said patient specific information, and a cart processor, wherein the cart drawers are filled with medicine from the medicine cabinet for each patient associated with each patient specific cart drawer in accordance with the respective physician order for each patient.

BRIEF DESCRIPTION OF THE DRAWING

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 11:
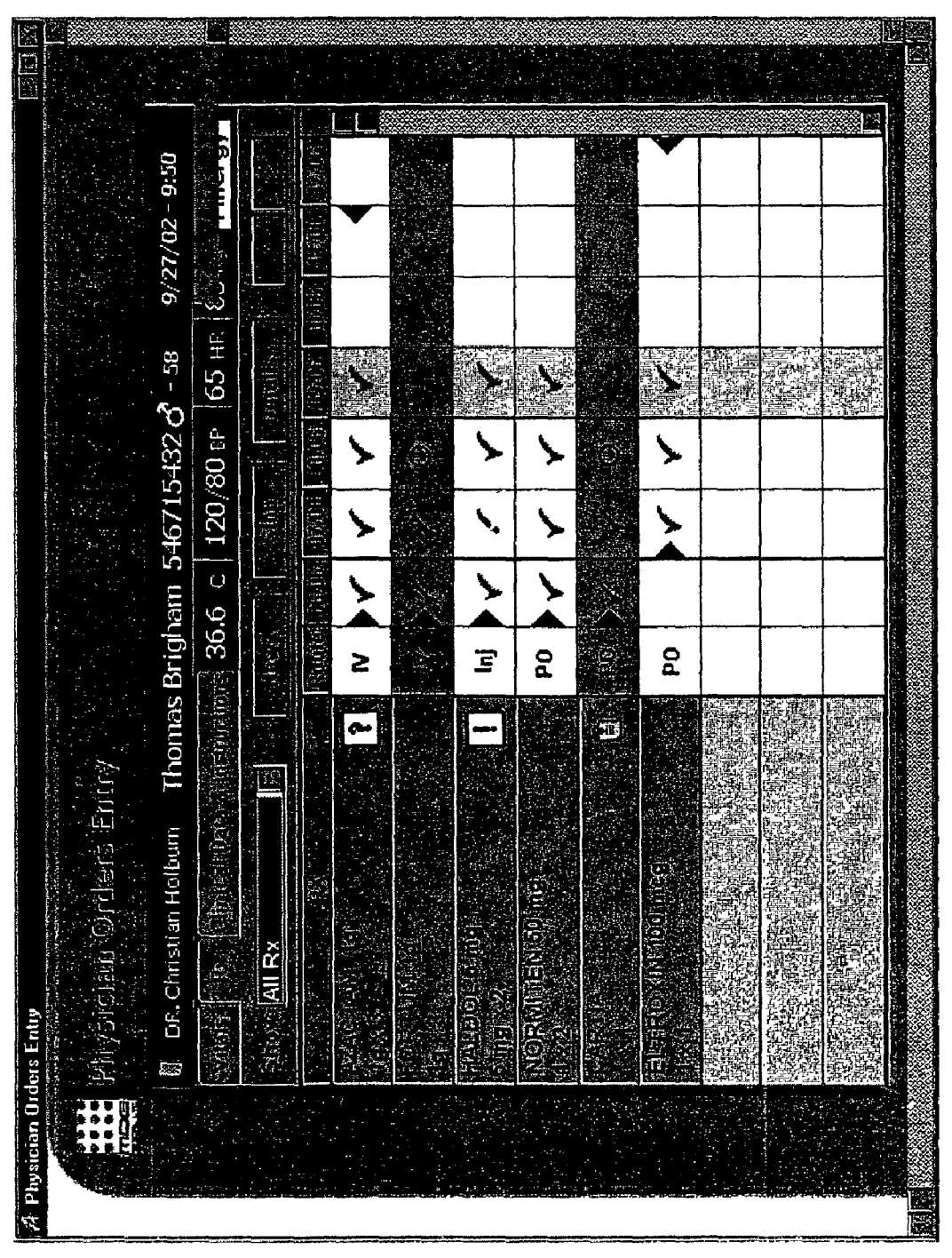

FIG. 11 is an exemplary illustration of a frame of the prescription program which allows a physician to review a patient's prescriptions in accordance with a preferred embodiment.

FIG. 13 is an exemplary illustration of a frame of the prescription program which displays details of a newly prescribed medication in accordance with a preferred embodiment.

FIG. 16 is an exemplary frame of the cabinet program which displays a patient's name, ID and medications to be administered.

DETAILED DESCRIPTION OF THE PREFERRED EMBODIMENTS

The Overall System

Figure 1:
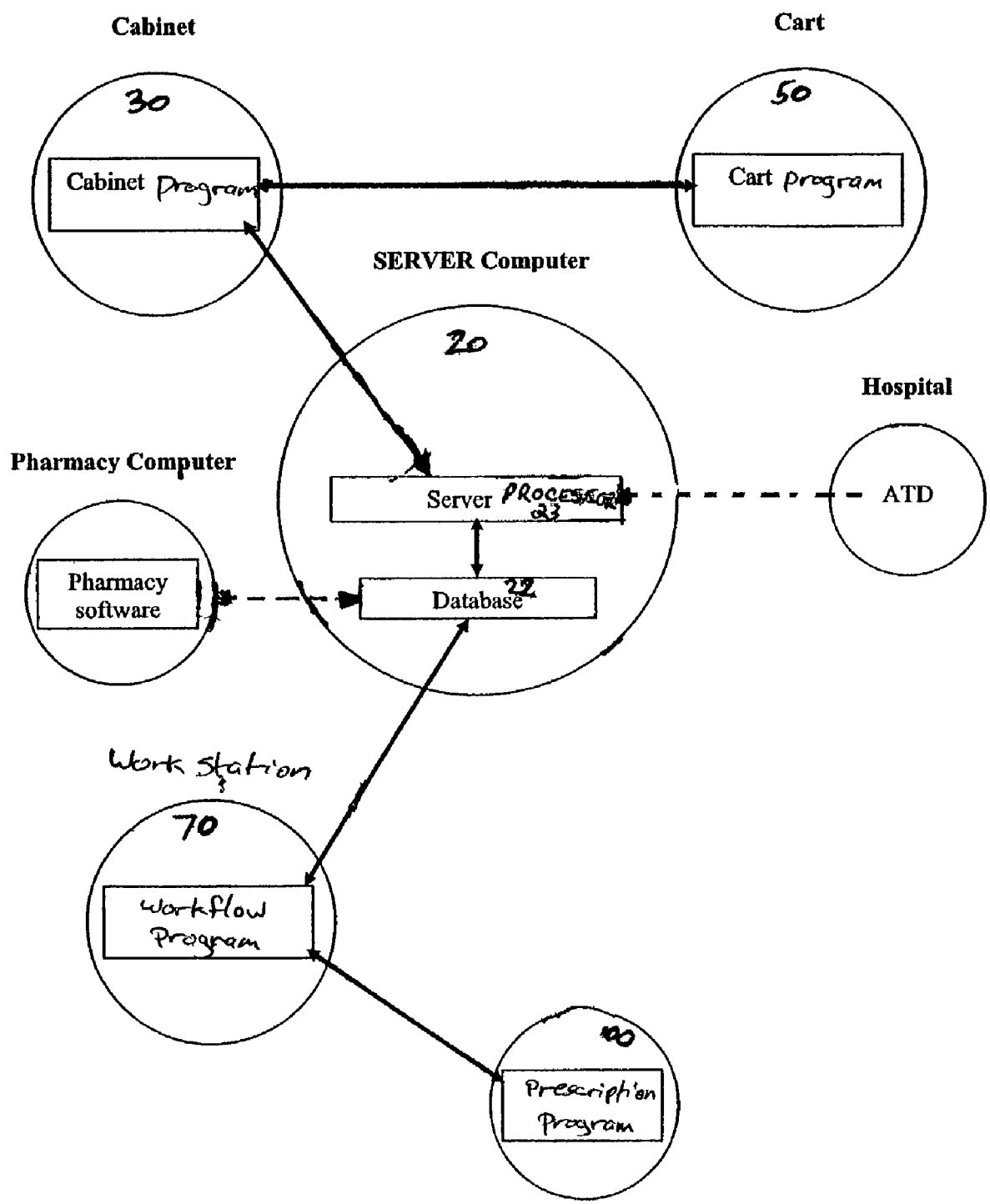
FIG. 1 is a block diagram illustrating the various components of a preferred embodiment of a medication dispensing system constructed in accordance with the present invention.

A preferred embodiment of the present invention will be described in relation to the drawing figures wherein like numerals represent like components throughout.

FIG. 1 is a block diagram illustrating the main components of a preferred embodiment of a medication dispensing system 10 constructed in accordance with the present invention as may be provided in a medical institution having one or more wards. The illustrated system includes a central server, generally designated 20, one or more work station(s) 70 for each ward; one or more medicine cabinets to serve one or more wards, generally designated 30, and one or more medication carts, generally designated 50. Each medication cart 50 is preferably adapted to accommodate a plurality of compartments, generally designated 51, 52, one or more for each patient in the respective ward and/or medication. System 10 further includes a plurality of hand-held, portable computers, each generally designated 60, for use by physicians, authorized personnel and/or pharmacists, when writing and/or authorizing prescriptions for individual patients.

As will be described more particularly below, a preferred system comprises server 20, medicine cabinet 30, cart 50, work station 70, and hand-held POE computer 60 enable information involved in the dispensing, replenishing and record-keeping operations to be performed electronically without requiring the attendant medical personnel to access to patient's written files. Such a system therefore minimizes the possibility of error, and also relieves the nurses or other healthcare attendants of many tasks required in the conventional medication dispensing system. In addition, described system 10 enables the healthcare attendants to enter vital signs of the patient into the records in order to provide updated information of the patient's medical condition.

Central Server

Central Server 20, provided in a medical institution, is coupled to medicine cabinet 30 and workstation 70 and comprises a database 22 and a server processor 23. It should be noted that a "medical.institution," as defined herein, includes elderly homes, hospitals and overnight medical facilities or clinics of all sizes, which administer medications on-site, such as those facilities having only a few beds, as well as hospitals having one or more wards, each ward having a plurality of beds. "Ward" is generically defined herein and means an institution or an area of an institution that is named for the type of patients that are admitted therein, for example, the maternity ward, cardiology ward and the like. Server 20 may also be coupled to a pharmacy computer and an institution's legacy system, such as a hospital information system (HIS), each to be disclosed below. It is known that an institution's legacy system includes patient information from institution labs, an Admission Dismissal Transfer (ADT) database, and the like.

Server processor 23, coupled to database 22, executes a server software program, which stores and transfers an electronic record of a plurality of predetermined events and automatically transmits and synchronizes system 10 and its components, (comprising cabinet 30, cart 50, one or more work station(s) 70 and one or more POE computer(s) 60). Events, as disclosed herein, refer to any action conducted by an authorized physician or healthcare attendant at a medical institution. Server processor 23 also transfers data transmitted from and data to be transmitted to medicine cabinet 30, the institution legacy system and/or the pharmacy computer between system 10 components, as will be disclosed in greater detail below.

Although, server 20 is preferably separate from other components, the functionality of server 20 may reside on a workstation 70. Workstation 70 will be disclosed in greater detail below. Also, although server 20 is shown to be coupled to cabinet 30 and workstation 70, in an alternative embodiment, server 20 may communicate with all system components through a wire connection or wireless RF or IR connection.

Medicine Cabinet

As disclosed above, server 20 is coupled to medicine cabinet 30 and work station 70. Information received by, and stored on, server 20 is transmitted to medicine cabinet 30 through a communication link 36 included in medicine cabinet 30. Medicine cabinet 30 is coupled to server 20 and medicine cart 50 and comprises the communication link 36, a control unit 33, which includes a cabinet processor 38 for accessing a cabinet program that operates cabinet 30, and a plurality of compartments 31 for storing, for example, supplies of the different kinds of medications to be accessed by a healthcare attendant, which are used for preparing individual dosages to be delivered to the respective patients. Medicine cabinet 30 further acts as a communication link between cart 50 and server 20 for recording information in server 20, e.g., vital signs of the respective patients as may be taken during rounds, as well as other information, as will be disclosed in greater detail below.

Figure 3:
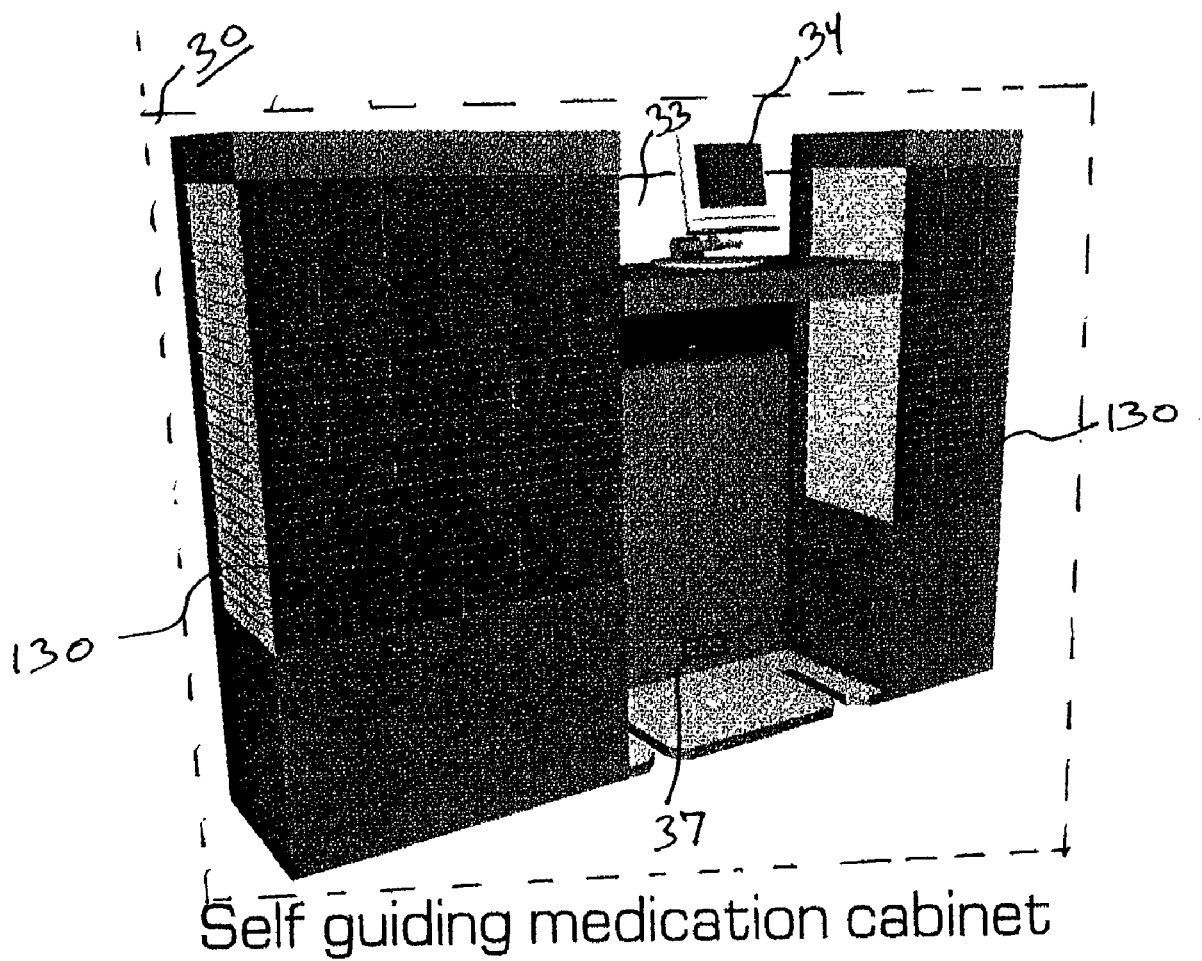
FIG. 3 is a diagram more particularly illustrating an exemplary form of a medicine cabinet in accordance with the preferred system of FIG. 1.

In a preferred embodiment of medicine cabinet 30, as shown in FIG. 3, cabinet 30 comprises a housing in which the medication compartments are in the form of drawers 31 arranged in an array 130, referred to herein as a frame, preferably comprising one or more horizontal rows and vertical columns. As shown, the housing is rectangular, and drawers 31 are arranged in a rectangular frame 130. However, medicine cabinet 30 need not be limited to a specific size or shape.

Each frame 130 is preferably organized according to different drawer sizes. It should be noted that drawers 31 of medicine cabinet 30 may be either medication-specific, patient-specific or a combination of medication and patient-specific. Those drawers 31 that are patient specific each comprise a display, such as an LCD display that displays the name of the patient assigned to the drawer 31. Each medication and patient specific drawer 31 also preferably includes a lock mechanism (not shown) which normally locks the drawer in its closed position, but which is selectively actuatable to unlock and spring forward the drawer to enable a pre-authorized healthcare attendant to access the medication supply within the drawer. An exemplary lock mechanism is illustrated in FIG. 4, but other such mechanisms would be known to one skilled in the art.

Figure 4:
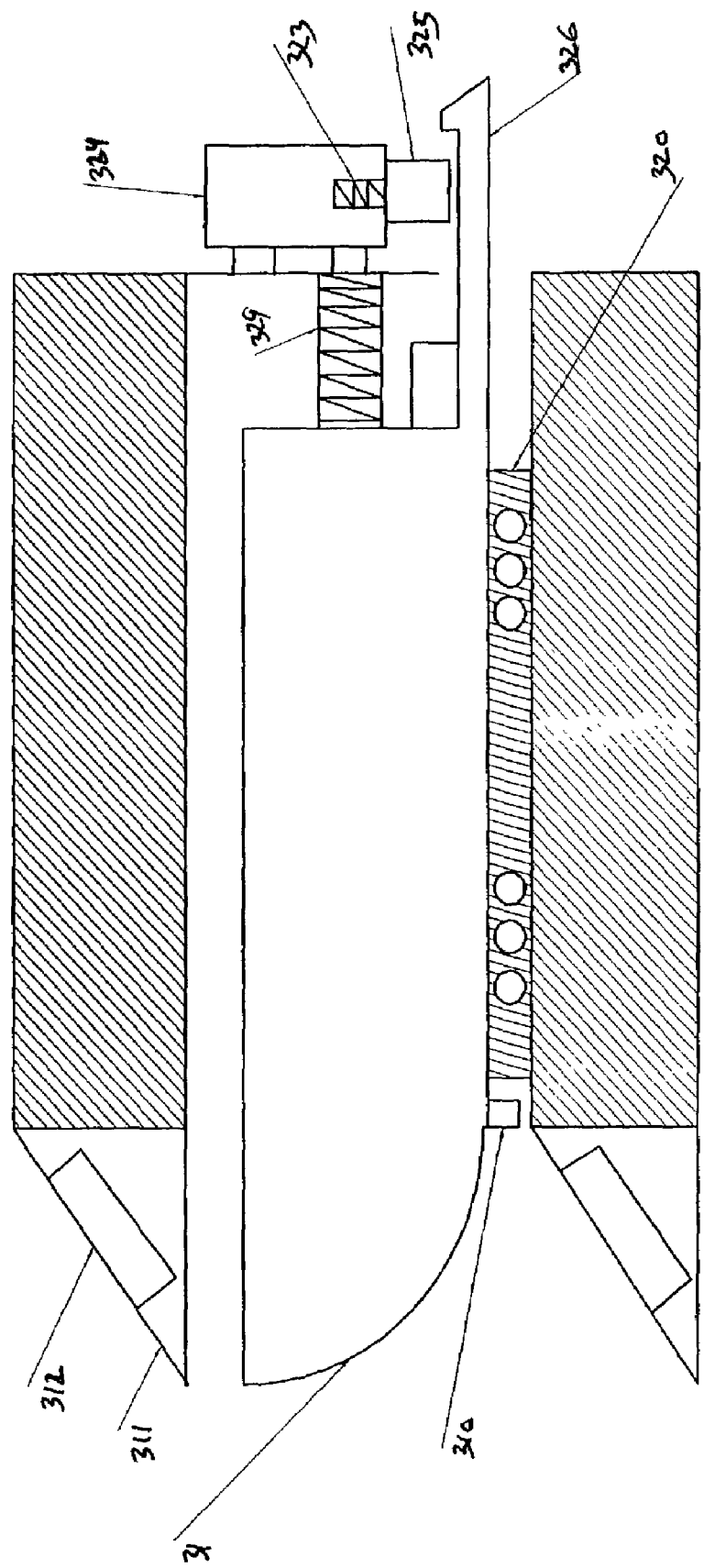
FIG. 4 is a diagram of a lock and spring mechanism in accordance with the preferred embodiment of the present invention.

As shown in FIG. 4, each lock and spring mechanism for each drawer 31 is activated by an "open" signal from the cabinet's processor 38, as will be disclosed in additional detail below. When the lock mechanism receives the "open" signal from processor 38, the lock mechanism springs drawer 31 forward, exposing the medication stored therein to the healthcare attendant who has opened the drawer.

As shown, the exemplified lock mechanism comprises a solenoid coil 323, a solenoid 324, a solenoid cylinder 325, a snapper 326, and a mainspring 329. However, any of a variety of lock mechanisms known to one of ordinary skill in the art may be used to maintain drawer security and operation as exemplified herein.

As shown in FIG. 4, exemplified cabinet drawer 31 comprises a drawer quick release mechanism 310 and a linear slide bearing 320. In operation, cabinet process 38 initiates an open signal and switches on a DC voltage supply (not shown) of 9–11 volts on solenoid 324. Solenoid 324 then applies a magnetic field on solenoid coil 324, which results in the movement of solenoid coil linearly upward. As solenoid coil 324 moves upward, solenoid cylinder 325 is pulled upward, releasing snapper 326.

Once snapper 326 is released, mainspring 329 springs drawer 31 forward. Drawer 31 is then opened allowing medication therein to be dispensed or medication to be placed therein, as will be disclosed in greater detail below.

After the medication is taken out of or placed into drawer 31 as required, drawer 31 is preferably pushed back to the closed position. As drawer 31 is being pushed back, snapper 326 is pushed against solenoid cylinder 325, which is being pushed up. Once the snapper clears solenoid cylinder 325, solenoid coil 324 pushes solenoid cylinder 325 downward, locking drawer 31 in its original locked position, whereupon snapper 326 is held in place by solenoid cylinder 325.

Referring back to FIG. 3, the exemplified and illustrated medicine cabinet 30 further comprises an integrated touch screen 34 coupled to control unit 33, a communication link 36 for linking to central server 20, and communication link 37 for linking to one or more cart(s) 50. Such communication links 36, 37 are schematically shown as connectors for wired communication, but could also be transmitters and receivers (e.g., RF, IR, acoustical) for wireless communication as would be recognized by one of ordinary skill in communication technologies. In addition to the data that is input via the communication links 36, 37, data is inputted manually via a virtual keyboard included in touch screen 34. Communication link 36 is a direct connection to server 20 and allows medicine cabinet 30 to interface with the database 22 on server 20, for real-time updates. It also facilitates providing necessary information to guide the pre-authorized healthcare attendant in the preparation of patient medications, intravenous solutions and the like, to be disclosed hereinafter. In an alternative embodiment, an actual keyboard or keypad may replace the functions of touch screen 34.

Information sent to and received from medicine cabinet 30 by server 20 is processed by server processor 23. In one preferred embodiment, the cabinet program is not directly compatible with database 22. Accordingly, server processor 23 preferably converts the information to a usable format for database 22 when transmitted from cabinet 30 and to a usable format when transmitted to cabinet 30. In another embodiment, the cabinet program is directly compatible with database 22, wherein server processor 23 stores the information until transmitted by cabinet 30 or database 22.

The foregoing components of medicine cabinet 30, illustrated in FIG. 3, are electrically powered, e.g., by a power supply, which preferably also includes a back-up unit in the event of power interruption or failure.

Such a cabinet 30 has a capability of accommodating a large number of different medications, although not all drawers or compartments 31 must be used at any point in time. If needed, however, a ward may be provided with more than one frame 130. Such an additional frame or frames 130*a* would provide additional drawers 31, but would include a cable connection to control unit 33 of cabinet 30 in order to enable each additional frame 130*a* to share its display 34.

It should be noted that the sections of the medicine cabinet configured for "special" medications, e.g., those medications too large for the medication or patient specific drawers, those requiring storage at a special temperature, and/or special protective measures to control access (IV fluids, refrigerated medicines, narcotics, etc.) may be provided in an additional frame 130*a*. In a preferred embodiment, frame 130*a* is specifically configured to support the "special" medications. For example, a frame 130*a* for medicine cabinet 30 may be configured to provide for the storage of "special" medications, along with the "non-special" medications. Where cooling is required, frame 130*a* includes one or more refrigeration unit(s). Where special security measures are required, such as for narcotics, a secure section of the array is secured by an additional locking system. For example, it may be unlocked only when a proper identification means, such as a valid password, a biometric identification or a personal identification is inputted using the touch screen 34 or keypad.

Although, the storage of "special" medications has been disclosed as being handled by an additional frame, storage may in the alternative be provided in frame 130 which may include a section(s) for storage of such special medications, or by other arrangements linked thereto. It is preferable, though, that refrigerated medications and narcotics reside in separate frames.

During a system failure only, an electronic backup system may be operated to open all the drawers 31 in cabinet 30, which then, in fact, transforms cabinet 30 into a completely manual cabinet. The backup operation is initiated, for example, by pressing a covered push button (not shown), which opens all the drawers 31 of a given frame 130. Preferably, access to the button is simple, with each frame 130 having a sliding cover that when open, unveils the push button. In an alternative embodiment, access to the button will be accessible only by a key or other manual unlocking mechanism.

In the event of an electrical system failure, system 10 will be backed up by a UPS system for several hours, which is very unlikely in patient care settings. If no electricity is available, the back of each frame 130 may be opened, and the drawers 31 released manually by a procedure that involves the release of a latch mechanism on each drawer 31, drawer by drawer, after which operation of the cabinet is completely manual.

In a centralized system, medicine cabinet 30 may alternatively be located in the central pharmacy, wherein all medications inventoried in the medical institution are stored. In this alternative embodiment, medicine cabinet 30 would operate in the same manner as disclosed above in the preferred embodiment and comprise a plurality of frames 130, 130*a*.

Although cabinet 30 has been exemplified and illustrated as a wired connection to server 20, another embodiment of cabinet 30 may include a wireless communication link between cabinet 30 and server 20.

Medicine Cart

As stated above, cabinet 30 is coupled to one or more medicine cart(s) 50 through communication link 36. In a preferred embodiment, medicine cart 50, as exemplified and illustrated in FIG. 5, comprises a plurality of compartments 51, 52, preferably in the form of drawers; a display or touch screen 54; a cart processor (not shown), a communication link 55 for linking to medicine cabinet 30; a keyboard 56, preferably a virtual keyboard on touch screen 54; a bar code reader 57; and a communication link 53 to monitoring equipment. In a preferred embodiment, cart 50 further comprises one or more chargeable batteries (not shown). In an alternative embodiment of cart 50, the monitoring equipment is a part of cart 50 or separate, but coupled to the cart processor through link 53.

The plurality of drawers 51, coupled to the cart processor, include a display screen 510, and are controllably locked by a locking and spring mechanism (not shown), such as the lock and spring mechanism 32 disclosed above and illustrated in FIG. 4. Each of drawers 51, 52 are adapted to receive medications for administration to patients. As exemplified and illustrated in FIG. 5, cart 50 comprises drawers 52 of differing sizes; the larger drawers 52 also being controllably locked by the locking mechanism, which is controlled by the cart processor. While cart 50 is not coupled to medicine cabinet 30 and in an idle state, display 510 of each drawer 51 is blank indicating that each of drawers 51 is unidentified, resulting in a generic medicine cart 50.

Preferably, cart 50 is in communication with server 20 through communication link 55 coupled to medicine cabinet 30. As exemplified and illustrated in FIG. 5, communication link 55 is preferably positioned in the lower rear portion of cart 50 in order to allow for the coupling of mobile cart 50 to medicine cabinet 30. Although communication link 55 is preferably located in the lower rear of cart 50, the communication link 55 may be positioned any place on mobile cart 50, so long as the link is accessible to medicine cabinet 30. Preferably, communication link 55 and communication 37 are coupled by a wire. In another embodiment, however, the coupling of communication links 55 and 37 is wireless, such as by an infra-red (IR) or radio frequency (RF) connection. It should be noted that communication link 37 of medicine cabinet 30 preferably includes a charger for charging the batteries (not shown) which operate cart 50 when the cart is in use away from medicine cabinet 30.

When cart 50 is coupled to cabinet 30 at the initiation of rounds, the cart program assigns one or more specific drawer(s) to each patient receiving medication during the rounds, resulting in the conversion of cart 50 from a generic medicine cart to a patient specific cart. For each drawer assigned a specific patient, the patient's name is displayed on the patient specific drawer display 510. Once the healthcare provider has finished the rounds, patient specific drawer display 510 for each patient is deleted, resulting in the return of cart 50 to a generic medicine cart. More specific information regarding the administration of medication to patients is disclosed below.

The cart processor, is coupled to bar code reader 57, the plurality of drawers 51, 52, touch screen 54, communication link 55, keyboard 56, and communication link 53. The cart processor accesses the cart program in order to operate cart 50 in accordance with a preferred embodiment. For example, the cart program assigns the drawers 51 to specific patients, controls the access to drawers 51, 52 and instructs the health care attendant in the filling of cart 50 and the administration of medications to the patients. Other functionality of cart 50 will be disclosed below.

Information transmitted to medicine cabinet 30 from server 20 is preferably transmitted to cart 50 through communication link 55. This information is utilized by the cart program to instruct the healthcare attendant in the administration of medications to the patients. While operating cart 50, the healthcare attendant is preferably required to log each event that is requested by the cart program and/or conducted by the healthcare attendant, e.g., taking of the medication by the patient, refusal of medication by the patient, absence of the patient, and the like.

Other information is also input to the cart program, such as real-time vital sign information. This information is taken by the healthcare attendant using the patient monitoring devices of cart 50, as disclosed above. For those devices that are located at the patient's bedside, communication link 53 facilitates the communication between the monitoring devices and cart 50, such as through a standard RS-232 link. This information is later transmitted to server 20.

Bar code reader 57, coupled to the cart processor, is preferably used to identify a patient, medication and dosage verification, and the like. When the healthcare attendant arrives at the patient's bedside, the healthcare attendant preferably scans the patient's wristband. The time at which this event takes place is preferably logged by the cart program and later transmitted to server 20.

Keyboard 56, which as indicated above is preferably a virtual keyboard, may be used as an alternative means of inputting patient information, as well as for inputting information required by the cart program as it relates to the administration of medication to the patient by the authorized healthcare attendant. Keyboard 56 may also be used to input any necessary identification means.

In an alternative embodiment, the cart program also controls the charging of the one or more rechargeable batteries, such that, when coupled to the medicine cabinet 30, the cart program determines whether the batteries need to be charged. If the remaining battery life of the batteries is below a predetermined level, the cart program activates the charging process. Otherwise, the cart program disengages the charging process, enabling efficient use of the cart batteries.

Figure 5:
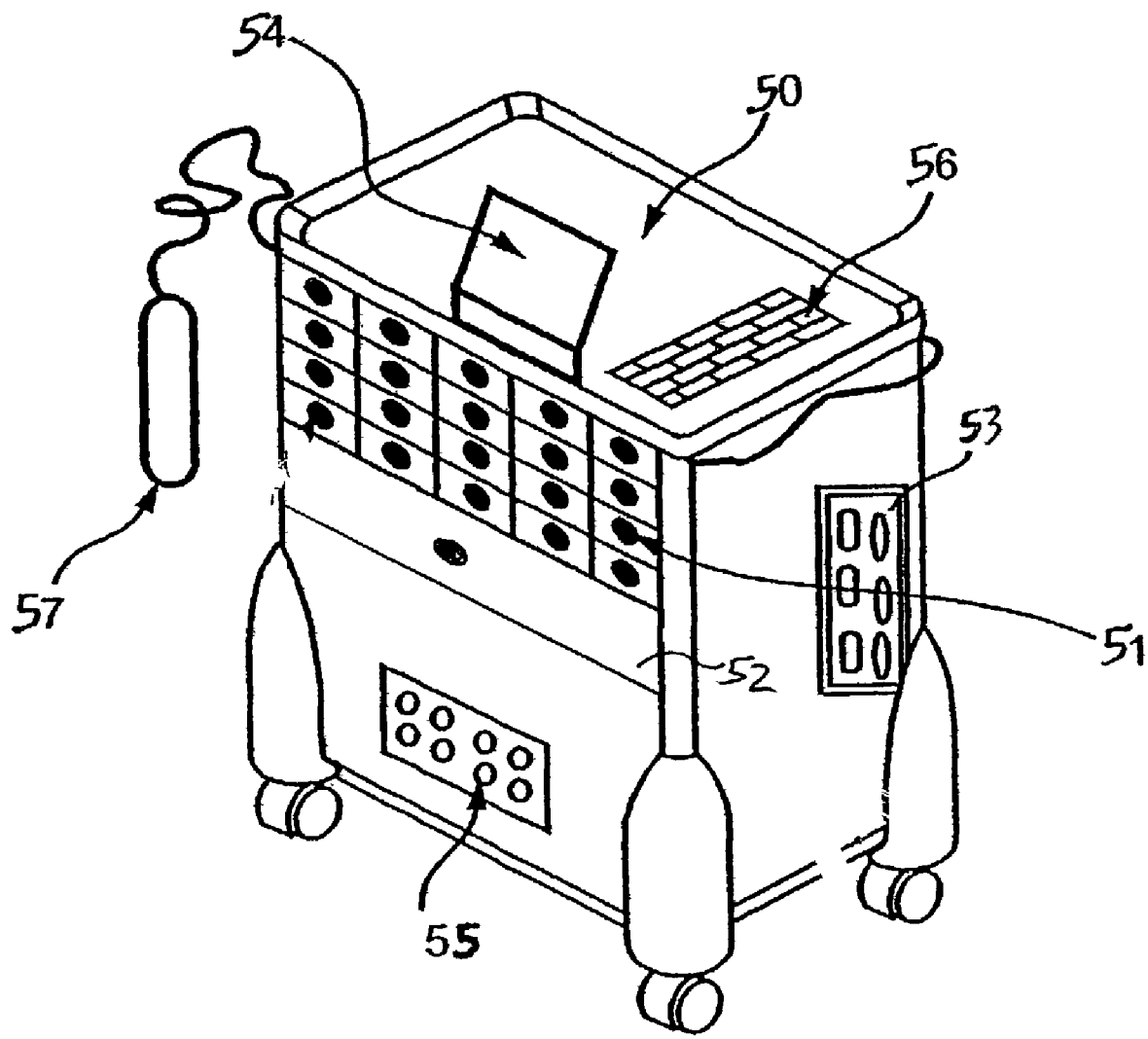
FIG. 5 is a diagram illustrating the construction of the mobile cart in the system of FIG. 1.

As exemplified and illustrated in FIG. 5 and stated above, the information stored in the cart processor is transmitted to server 20 through communication 55 to link 37 of cabinet 30. Similar to cabinet 30, the information transmitted by cart 50 is processed by server processor 23 and stored therein until database 22 retrieves the information therefrom. In another embodiment, the information transmitted from and transmitted to cart 50 is compatible with that which is stored in database 22, wherein the information is directly transmitted to, or transmitted from, database 22.

Although cart 50, in a preferred embodiment, is illustrated and disclosed as communicating with server 20 through cabinet 30, in another embodiment, cart 50 may communicate directly with server 20 through a direct network connection or through a wireless IR or RF connection. Cart 50 may alternatively communicate with cabinet 30 through a wireless IR or RF connection.

The preferred embodiment of cart 50 allows the healthcare attendant to log real-time information related to drug administration at the point-of-care (i.e., at the patient's bedside), resulting in accurate and complete information.

Although cart 50 has been disclosed as communicating with server 20 through cabinet 30, in an alternative embodiment, cart 50 communicates directly with server 20 using a wired communication means on a wireless IR or RF communication means.

Work Station

Referring back to FIG. 1, one or more workstation(s) 70, coupled to server 20 and hand-held Physician Order Entry (POE) computer 60, preferably accesses a workflow program that supports management and operational functions including time related tasks, pharmacy and inventory control and intelligent decision capabilities to aid the physicians and health care professionals. It should be noted that the term "physician order entry" computer is generic and should not be used to limit either the location of the computers or who may use the computer. The term "workstation" is also generic and means a single computer at a single location, a plurality of computers at a plurality of locations, and/or a plurality of computers at a single location. Accordingly, when the term workstation is used herein, it should not be limited to any one definition.

Figure 2:
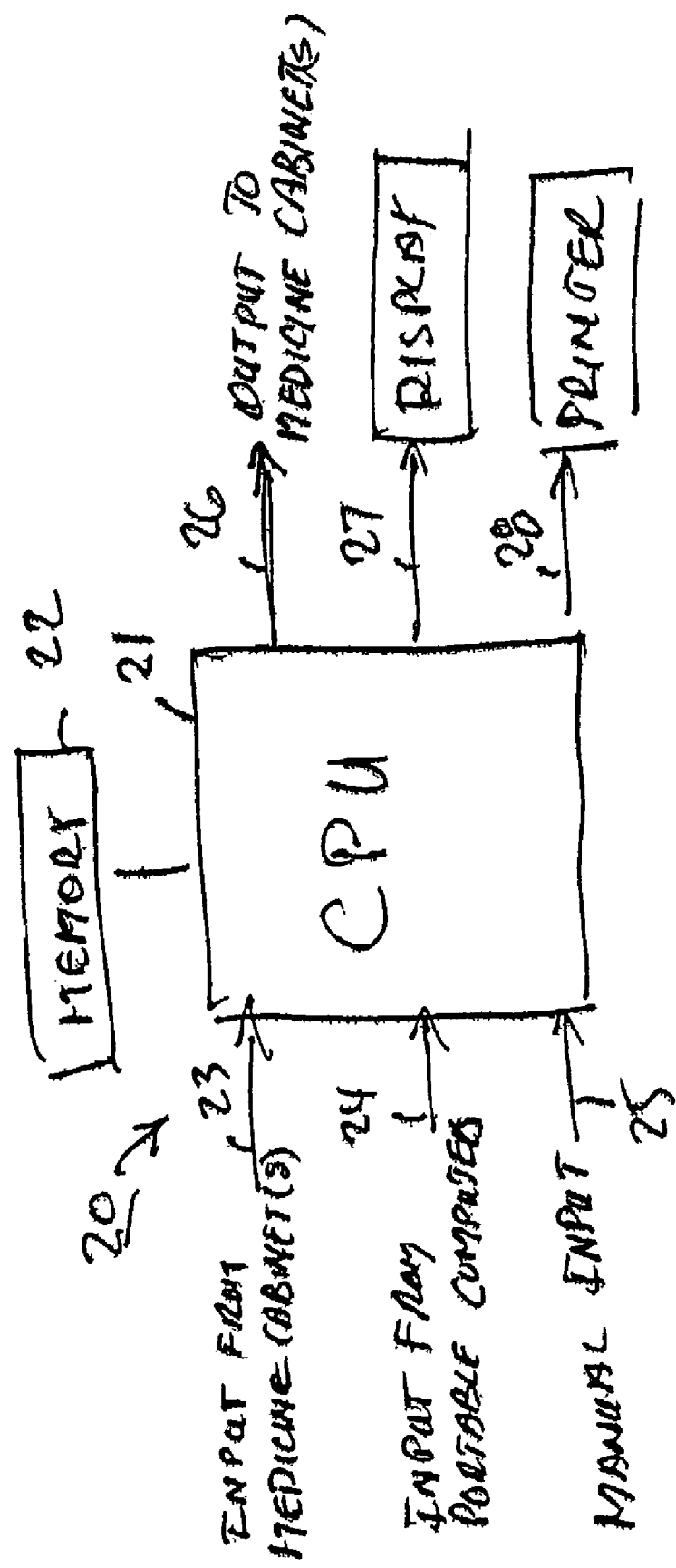
FIG. 2 is a block diagram illustrating the central (or ward) computer in accordance with the preferred system of FIG. 1.

FIG. 2 is a block diagram illustrating the main components of workstation 70 as would be provided in a ward, group of wards, nursing station(s), an office, and the like. Workstation 70 includes a conventional CPU (central processor unit) 71; an input 74 from handheld POE computer 60 (FIG. 1); an input 79 from an I.D. badge or other identification reader; and one or more manual inputs 75, such as a keyboard, touch screen, mouse, and the like. The workstation processor 71 includes an output a display 77 and a printer 78, e.g., for printing inventory records, patient medical records, physician orders, management reports, etc. The workstation 70 preferably does not have a direct output to cart 50 since it communicates with cart(s) 50 via server 20. Alternatively, however, when the functionality of server 20 resides on a workstation 70, a direct link to cart(s) 50 may be provided, such as through a wired connection or wireless IR or RF connection.

A main task of the workflow program is to manage (open, update and store) all patient entries for a respective ward, with every entry comprising, for example, the following information for each respective patient: name; identification corresponding to a bar code printed on the wristband worn by the patient; referring and treating physicians; relatives; allergies; medication orders, including an electronic signature or other electronic means by both the physician and/or the authorizing pharmacist; the vital signs of the respective patient as collected and stored during rounds, e.g., during a vital signs round and/or medication dispensing round; information about all medications prescribed and delivered to the patient while he/she is in the respective ward; and additional information that may be required by an institution. These patient entries are preferably opened, updated and stored in a database, such as a Medication Administration Record (MAR) and Mini-Patient's Medical Record (MMR). The patient entry also includes a status flag indicating whether the respective entry is active or deactivated (e.g., by the release or transfer of the patient to another ward or by discharge of the patient). The MAR and MMR databases preferably allow system 10 to access patients that have been discharged from the institution. In a preferred embodiment, preferably this information is retrieved from an Admission Dismissal Transfer (ADT) database, known in the art, located on the institution's legacy system.

When a patient is admitted, a healthcare attendant logs the patient's name and information into the institution's legacy system. The patient's information is then preferably transmitted to server database 22 for retrieval by the workflow program. Provided with the above information, as well as physician order entries for patients in the ward, the workflow program actively schedules and alerts clinical staff regarding the administration of medication, inconsistencies with data for prescriptions, and the, like.

The workflow program allows an institution to set authorization levels. For example, an institution may implement a hierarchical authorization scheme, wherein healthcare attendants are granted access to conduct certain tasks based in part on their level of experience, level of employment, and the like, e.g., a doctor may have access to prescription operations, to work station 70, and medicine cabinet 30, whereas an entry-level nurse may only have access to medications in medicine cabinet 30 that are non-narcotic. The scheme and rules used by the workflow program are determined by the institution. Alternatively, the scheme and rules may be embedded in the workflow program based on industry standards or a medical institution's predetermined policy.

The workflow program also permits a hierarchical set up regarding individuals with the authority to authorize others to have access to certain components or operations within system 10, and therefore allows input by the individual with the authority to authorize. For example, the head nurse may have the authority to allow or deny access to another nurse under his/her supervision. As above, this hierarchical scheme is determined by the medical institution's policy.

In accordance with a hospital's policies, work station 70, in various embodiments using the workflow program, also manages on-demand medications, such as stat medications, and PRN (per re nata), per request, medications. This necessitates opening certain drug specific drawers, and permitting the immediate administration of medications to a patient, even though a prescription may not have been issued. Authorization for the dispensed on-demand and PRN medication is subsequently requested to provide the necessary record of the action. As disclosed above, when the medication is administered to the patient, the healthcare attendant is preferably required to log the event and the reason therefor.

The workflow program also independently calculates and maintains a running inventory of the contents of medicine cabinet 30, including, for example, a special count for narcotic medications. Such inventories are continuously updated as the medications are dispensed and logged by the healthcare attendant, and as the medications are replenished and logged. The workflow program also maintains a list of the different kinds of medications and their locations in the matrix of drawers in the respective cabinet. Workstation 70 also assists in stock management, allowing for the addition of a new medication to be dispensed, or the removal of a medication no longer required. For example, computer 70 manages "multiple use" medications, e.g., bottled medications, eye drops, ointments, and the like, such that as the medications are assigned and used by a patient, computer 70 ensures that the proper amount of medication is remaining for the patient's subsequent use, and will notify the attendant accordingly.

Also, the workflow program assists in the maintenance of common stock medications which may be assigned and administered to a patient. As those skilled in the art know, common stock medications are routinely maintained in medicine cabinet 30 for administration to a patient. Common stock medications may include, but are not limited to, "multiple use" medications, as well as over the counter drugs, such as eye drops and bottled syrups. Accordingly, a common stock medication is assigned to a patient when authorized by someone authorized to prescribe such medication. For example, eye drops may be commonly stocked in medicine cabinet 30. When a patient is prescribed the eye drops, the workflow program transmits this information to the cabinet program which assigns the eye drops to the patient and instructs the healthcare attendant to place the eye drop container in the patient specific cabinet drawer 31, or instructs the attendant to bar code the eye drop container with the patient's patient ID and leave the eye drops in the common stock drawer.

For first dose medications that fall outside of the regular administration rounds or stat medication for a patient, the prescriptions for such medications may be filled at cabinet 30 through workstation 70. This eliminates problems associated with physicians telephoning in prescriptions, with accurate maintenance of the medication inventory, and efficient time management, thereby getting the medication requested to the patient in a fast and safe manner.

The management of the expiration dates for medications stored in medicine cabinet 30 is also done by the workflow program. Preferably, all medications stored in medicine cabinet 30 have been bar coded, scanned and stored by the workflow program, wherein the bar code includes, at least, the expiration date, batch number and name of the medication. Alternatively, the expiration date, name and batch number of the medication is inputted to the program manually using keyboard 75 as will disclosed below. The workflow program, then, automatically checks the expiration dates of all medications stored in medicine cabinet 30. An authorized healthcare attendant is warned through workstation 70 and an alert sounded at cabinet 30, when a medication is nearing the expiration date.

The workflow program also produces, if so requested by an authorized attendant, a wide variety of reports and records, including, but not limited to: current inventories in each ward cabinet, e.g., graphical displays of inventory levels, as well as the display of consumption of each drug over time and discrepancies in inventory count; the replenishing level of each medication; information concerning patient files, individually and collectively; information concerning patient vital signs, e.g., for graphic display; information regarding all dispensing and replenishing of medications from the medicine cabinets, including date, time, names, and the like; replenishing forms to be directed to the pharmacy for replenishing a medication (a task which can also be performed by linking to the pharmacy computer); forms for emergency medication; and summaries of all the medications received by a particular patient during the stay in the respective ward, including billing, etc. This capability of the workflow program further supports patient accounting and reimbursement.

As indicated above, the workflow program provides, for example, the inventory of medications and their locations in cabinet 30, the names of the patients and their prescribed medication dosages; the type and quantities of medications as dispensed and as replenished; and the vital signs data with respect to the patients, each of which is inputted manually during a routine check by a nurse or other health care practitioner, such as physical therapists, inhalation therapists, radiologists and the like, or by a pre-authorized individual dispensing a medication to the patient.

It should be noted that a medical institution may utilize more than one work station 70, wherein each workstation 70 is coupled to server 20 and provides authorized users with access to the workflow program. When a plurality of workstations 70 exist, they may be located in one area or spread throughout the medical institution. For example, a work station 70 may be located at a nursing station in the maternity ward, as well as in the office of the head nurse of the same ward, or each nursing station in each ward of an institution may include a work station 70, etc. Nevertheless, for the purposes of this disclosure, if a plurality of workstations are used, they will be referred to herein simply as "work station," so long as each of the plurality is linked. Hospital policy preferably dictates how many work stations 70 are included in system 10, who is authorized to access the work station 70, and his/her level of access to the information provided therein.

POE Computer

Figure 6:
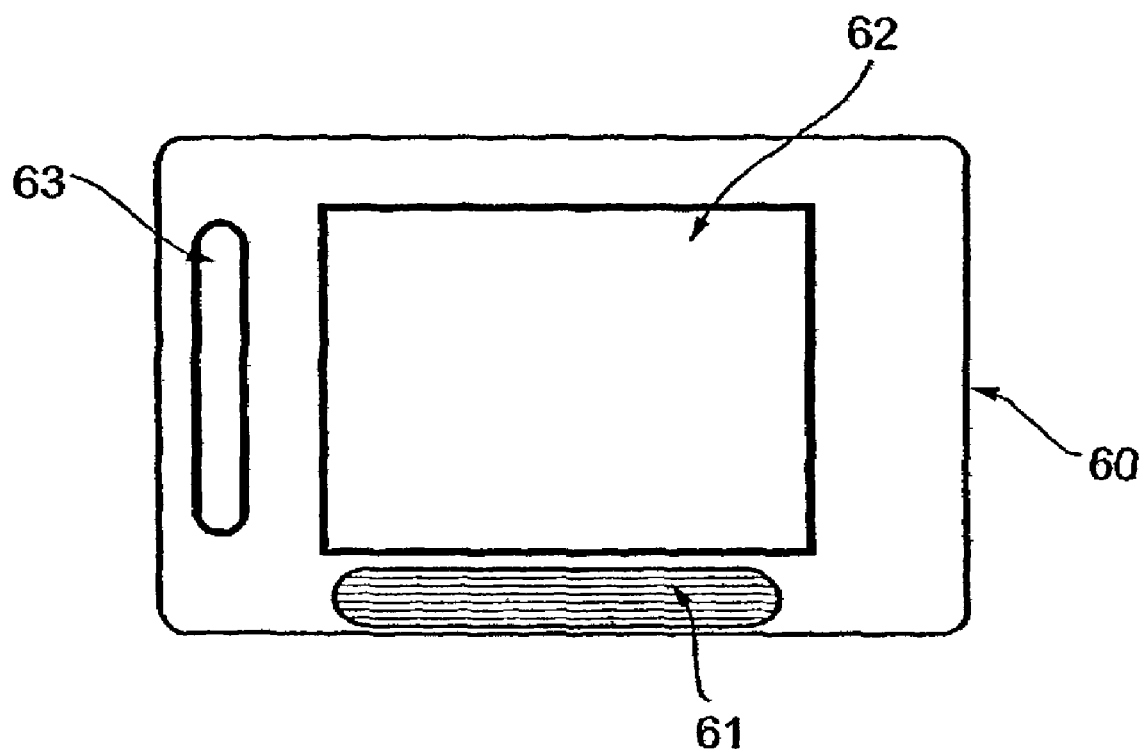
FIG. 6 is a diagram more particularly illustrating the portable computer for the physician and/or pharmacist in the system of FIG. 1.

A system for the safe and efficient administration of medication requires a computerized patient file containing, at least, the details of the patient and the medication the patient is to receive. This data may be hand-entered in the server 20 through work station 70, from hand-written notes, e.g., prepared at the time of the physician rounds. However, in a preferred alternative a hand-held POE computer 60, is illustrated in FIG. 6, which includes prescription software to allow the physician to prescribe medications at the point of care (i.e., at the patient's bedside).

As indicated above, POE computer 60 is preferably coupled to workstation 70. POE computer 60 includes a large display 62, preferably of the touch screen type to enable inputting information, and a communication link 63, which may be wired or wireless, to establish communication with server 20. In an alternative embodiment, hand held POE computer 60 further comprises a bar code scanner, for identifying a patient to be examined. Such POE computer 60 executes a prescription program that allows the physician to prescribe medications through the system, or change the medications or their dosages, and check drug interactions and patient allergies at the time of prescribing. Preferably, a commercial product, such as First Data, is utilized to verify drug interactions after a medication is prescribed by the physician for a patient. The validation program informs the physician regarding any negative interactions. The prescription program also facilitates the receipt and retention of the physician's, and/or the pharmacist's electronic signature or other electronic identifying means, together with the rest of the data collected.

The prescription program alternatively allows the institution, in accordance with the institution's policies, to limit the physician's ability to prescribe certain medications. The limitations may be based on the economics of dispensing a certain medication as compared to a similar medication, or inventory in the institution, for example. It is preferable for this alternative to allow the physician to override the limitations by the institution when he/she see fit, as long as the physician explains the reason for the override, which explanation is prompted by the prescription program. The prescription program will time and date stamps the explanation and store this information.

At the end of the rounds, the hand-held POE computer 60 may be coupled to work station 70 through input 24 to permit the transmission of all of the information collected in the hand-held POE computer 60, including the electronic signature or other electronic identifying means of the physician and/or pharmacist. This information is entered into the record of each respective patient by the prescription program. Hand-held POE computer 60 may also be used for entering and/or displaying patient specific information, for example, the vital signs, sensitivities, drug interactions and any other pertinent data taken while the patient is hospitalized.

Hand-held POE computer 60 and its ability to link to the program significantly reduces human error due to transcription and poor legibility, and helps reduce insurance and liability costs to the physician and institution.

In an alternative embodiment, the functionality of each component program may be accessed by any other system 10 component. For example, the workflow program may be accessed by medicine cabinet 30 or POE computer 60. When the scheduler of the workflow program alerts medicine cabinet 30 of the start of a round, medicine cabinet 30 accesses the cabinet program and the workflow program.

Although system 10 has been disclosed in accordance with a preferred embodiment illustrated in FIG. 1, any one of the components of system 10 may communicate directly with any other component by wireless communication such as RF or IR communication means, wherein each components comprises a means of communicating in a wireless environment.

Operation

The described system 10 may be used in performing a number of processes including, but not limited to the following:

Initial Data Entry

As indicated above, each of the disclosed components is coupled to ward computer 20, providing a closed loop computerized work flow system which manages the patient care including, for example, including, for example, prescribing to the dispensation, administration and reporting of activities.

When a patient enters the medical institution (i.e., for admission to the extent that drugs or medications will be administered to the patient), patient information is preferably entered into the institution's legacy system by an authorized healthcare attendant or via interfacing with patient information already stored in a central admissions system, such as the ADT described hereinabove. The institution legacy system transmits the ADT information for the admitted patient to system 10. The patient information includes demographic information, which is then included in a patient file. Once the patient file is opened, a bar code is preferably generated using the institution's patient ID, generated by the legacy system during admission, or using a patient ID generated by system 10, which is indicative of a patient code that is associated with the patient. A print signal is preferably sent to a printer (not shown). The printed bar code is then preferably placed on a wrist band that the patient wears on his/her wrist until discharge from the ward. This patient code is preferably used as the means of ensuring the accuracy of the identification of the patient by any of the healthcare professionals.

Figure 7:
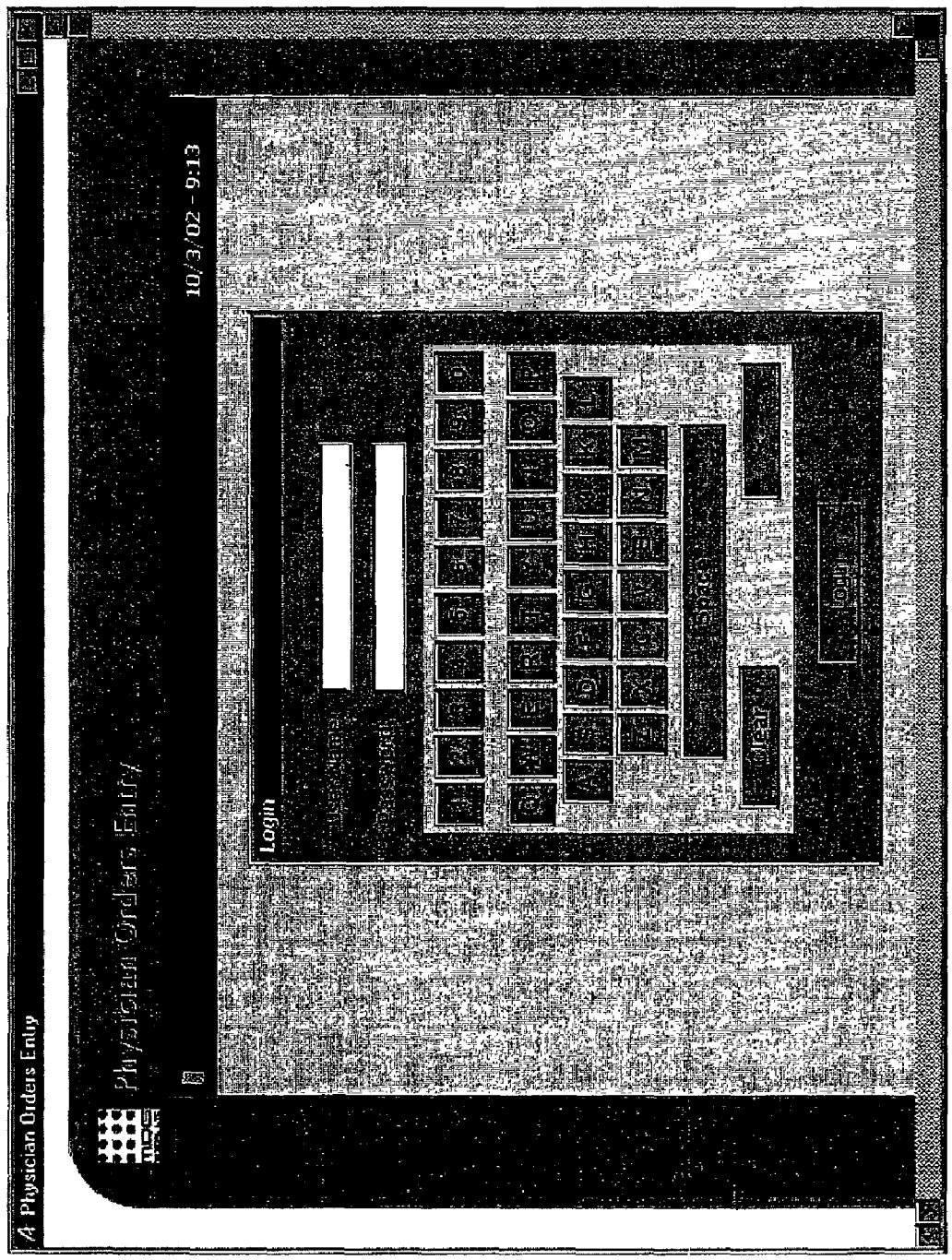
FIG. 7 is an exemplary illustration of a frame of the prescription program which allows a physician to input his/her authorization information in accordance with a preferred embodiment of the present invention.
Figure 8:
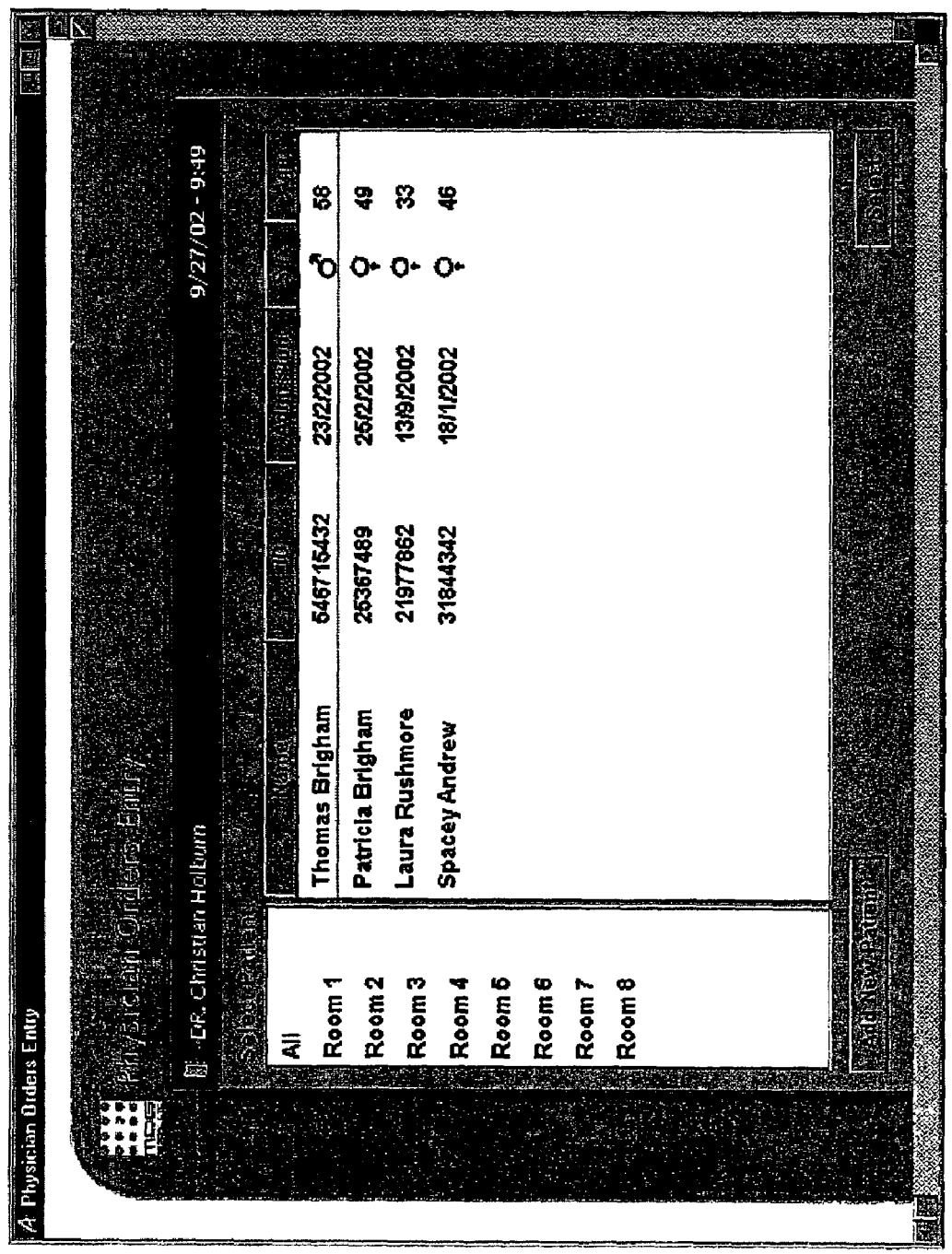
FIG. 8 is an exemplary frame of the prescription program which illustrates a list of patients in accordance with a preferred embodiment.
Figure 9:
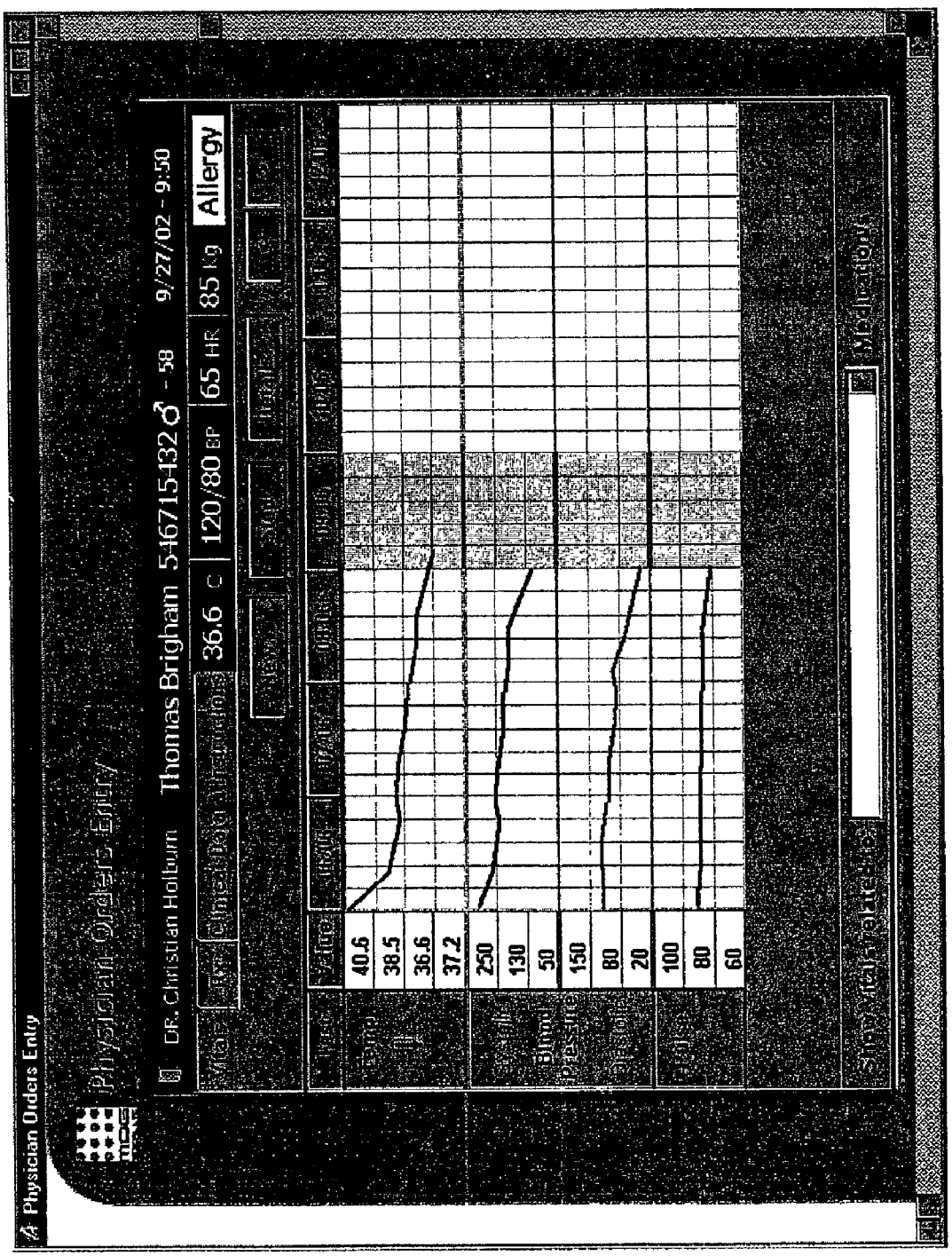
FIG. 9 is an exemplary frame of the prescription program which is a graphical illustration of the vital signs of a patient in accordance with a preferred embodiment.
Figure 10:
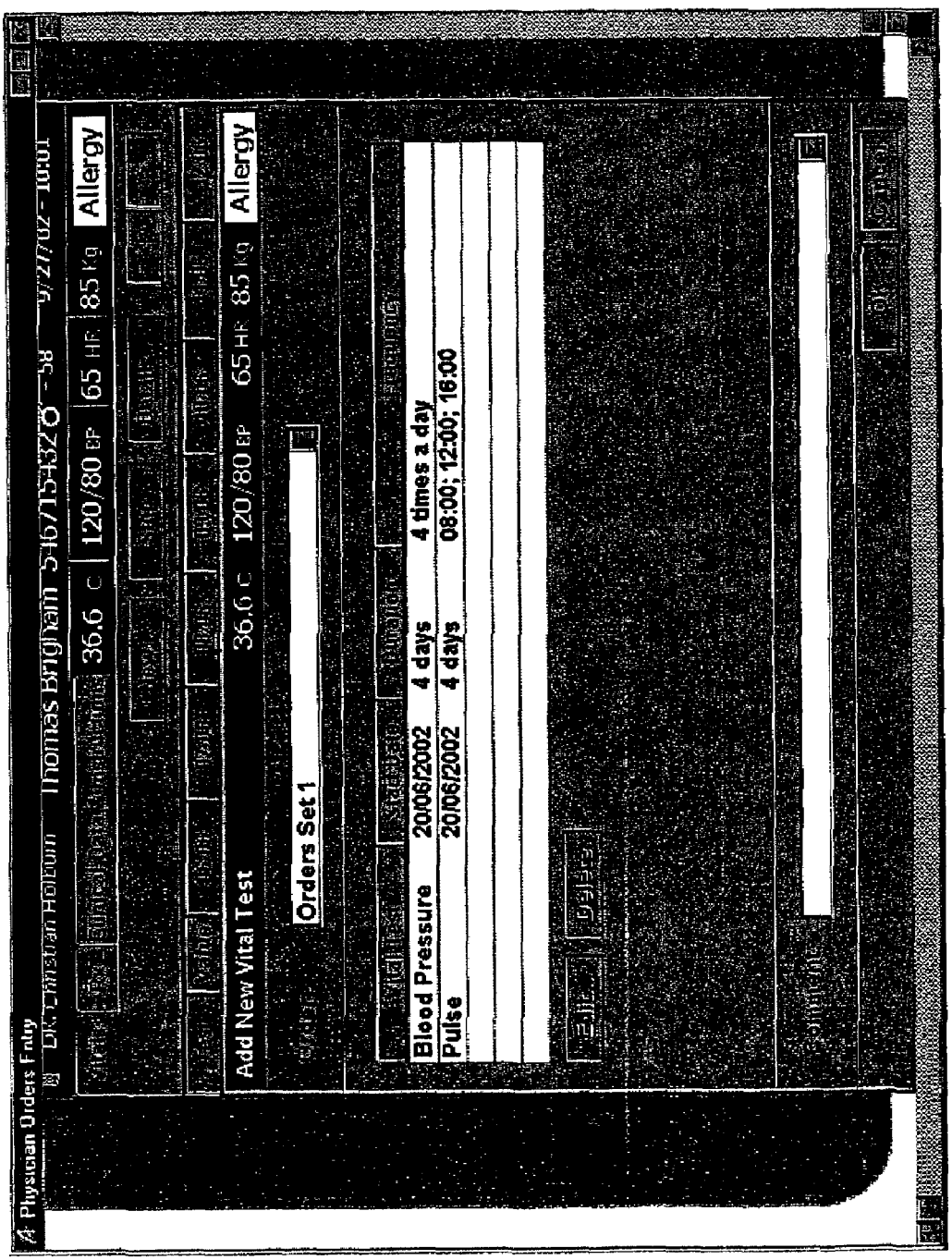
FIG. 10 is an exemplary frame of the prescription program which is a tabular illustration of the vital signs of a patient in accordance with a preferred embodiment.

A treating or attending physician on rounds, for example, preferably uses POE computer 60 as disclosed above to review the information therein in order to evaluate a patient's current condition. For example, when the physician arrives at the patient's bedside, the physician logs onto the POE computer 60 by entering in his/her authorization information using an identifying means disclosed above. An exemplary frame of the handheld POE computer 60 for entering the physician's authorization information is illustrated in FIG. 7. Once the physician has logged onto handheld POE computer 60, a list of patients is displayed by room number, in alphabetical order, or those patients attended to by the physician, for example, as exemplified in FIG. 8. The physician then chooses the patient's name of the patient he/she is attending or scans the patient's wrist band, automatically selecting the patient. The selection of the patient's name results in a display of the vitals and information for that patient, which have been previously input by an authorized attendant or physician. An illustration of an exemplary frame showing graphical and tabular vital information is shown in FIGS. 9 and 10. Each of these exemplary frames also comprises multiple keys or tabs.

As exemplified in FIG. 10, the physician may then choose to review the patient's current prescriptions and his/her respective details by selecting the RX tab. The physician may also choose to view the clinical data and instructions by selecting the appropriate tab on the screen, which displays that information, for example, the patient's allergies and symptoms.

Figure 12:
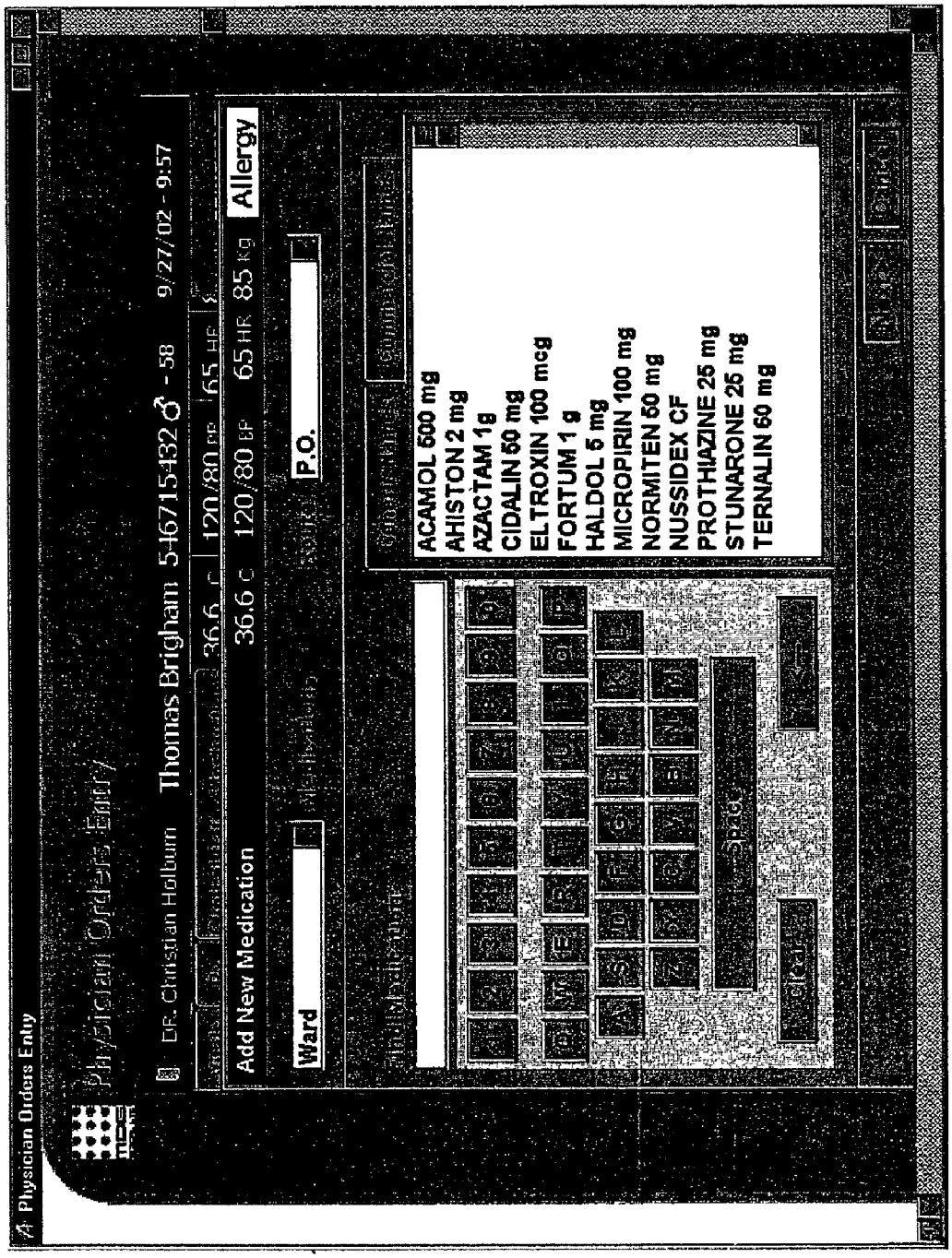
FIG. 12 is an exemplary illustration of a frame of the prescription program which allows a physician to add new medications to a patient's prescription in accordance with a preferred embodiment.

The physician is able to find and prescribe new medications for the patient using the RX tab as illustrated in FIG. 12. As stated, a physician is able to review the medications a patient is currently taking by selecting the RX tab which frame exemplified in FIG. 9. Once in the RX tab, the physician is able to view the details for each prescribed medication. This tab also provides the physician with a means of prescribing a new medication.

To prescribe a new medication, the physician first selects the "new" button included in the exemplary RX frame. As a result, for example, an Add New medication frame is displayed, such as that which is illustrated in FIG. 12. Although not shown in FIG. 12, a physician may choose medications from multiple listings. For instance, illustrated in FIG. 12 is a list of generic medications that are located within the hospital that the physician may choose from if the patient is required to have generic medications due to insurance restrictions, if the patient requests generic medication to be used, or if a physician requests a generic medication in accordance with hospital policy. The physician, though, may choose to prescribe brand name medication that is equivalent to the generic drug, in which case, the physician may select the "Commercial Names" tab to view a list of brand name medications. For those medications that are rarely prescribed, the physician may select from a national database that includes all medications available for prescribing, such selected medications would then have to be ordered. For those medications located in the inventory of the hospital, the physician is able to filter a list based on the location of the medication, e.g., ward or pharmacy, whether it is a special medication or an order set. Although the medications have been listed by name, it should be noted that the medications can be listed by system, e.g., nervous system, respiratory system, etc.

As described above, the POE computer 60 allows the physician to prescribe medication in accordance with a hospital policy that has been set up to ensure that the prescribed medication is the best medication for the patient and most economical for the hospital. Accordingly, the POE computer 60 preferably provides the physician with the recommended medication to be prescribed in response to the physician's selection. If permitted by the hospital, a physician may override the recommendation of computer 60, and prescribe the physician selected medication. If the physician is unable to override computer's 60 recommended medication, the recommended medication is prescribed.

Figure 13:
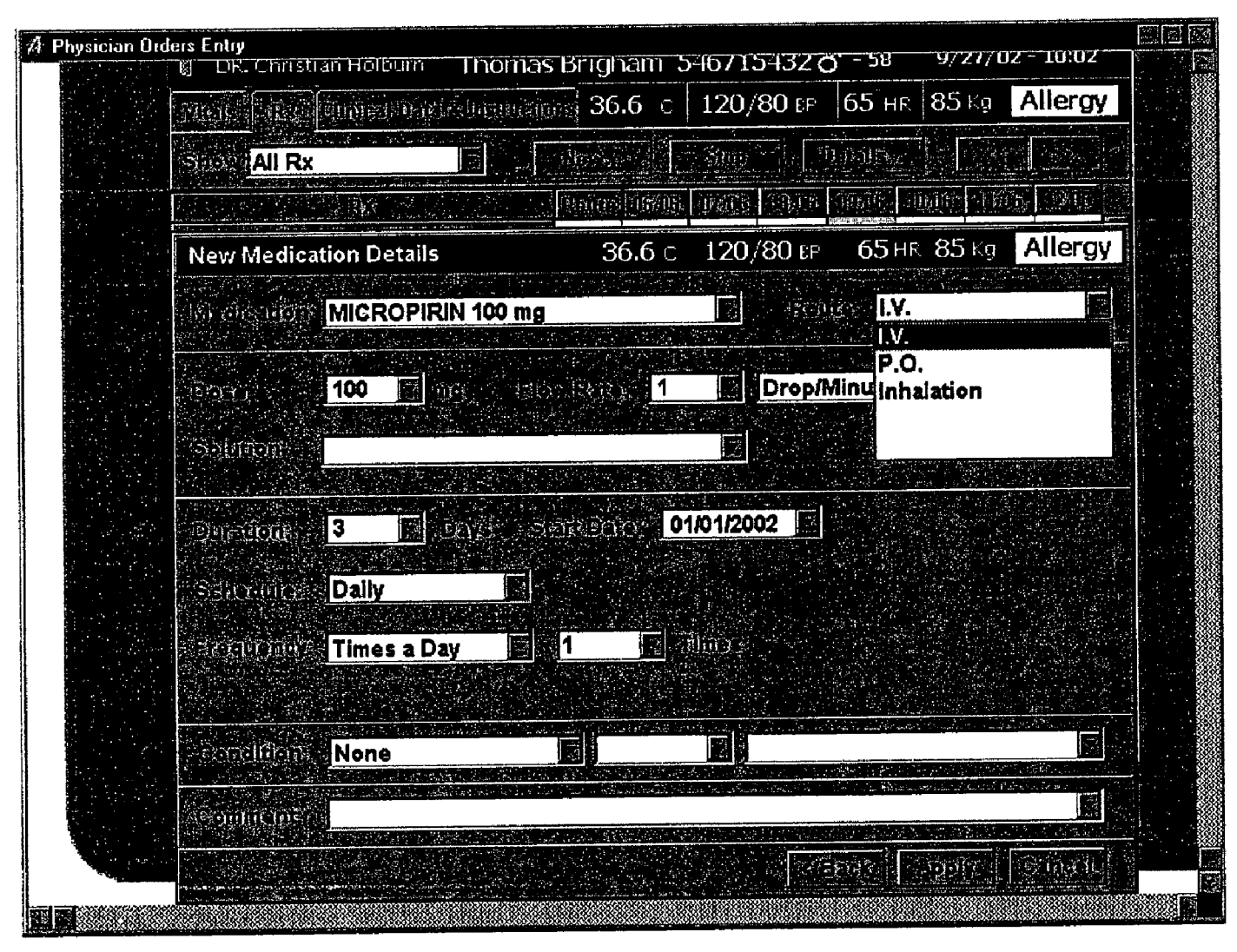

Once the physician has selected the medication, the physician preferably must enter the details of the order of the administration of the medication, such as dose, duration, schedule and frequency, as well as other pertinent information that will be used by the authorized healthcare attendant. The physician may also use defaults that are set by the hospital, which include the medication dose, duration, schedule and frequency. Also, treatment protocols may be prescribed by the physician, which may comprise several different medications and other orders, such as fasting, and the like. For example, after hip surgery, a patient may receive a predetermined medication and diet regimen that is used for most hip surgery patients. An example of the frame for entering the details of the newly prescribed medication is illustrated in FIG. 13.

Once the physician has completed the examination of the patient and prescribed the necessary medications, the physician may then exit the Add Medication frame. Upon exiting, POE computer 60 conducts a clinical screening of the medications prescribed for the patient and verifies that there are no known negative interactions between medications and that there are no known negative interactions between the medication and the patient's allergies or safety concerns. A typical and commonly used and accepted database for such procedure is, for example, First Data Bank or Micro Medics. The order entered by the physician is then automatically compared against predetermined standards to assure that the dosage is correct, and undergoes screening against the patient's medical history, including drug allergies and multiple drug interactions. It should be noted that the physician may look up the drug interaction, and side effect while prescribing medications by selecting this option on POE computer 60. Nevertheless, even if this option is selected by the physician, a check is automatically conducted after prescribing all medications for the patient.

Figure 14:
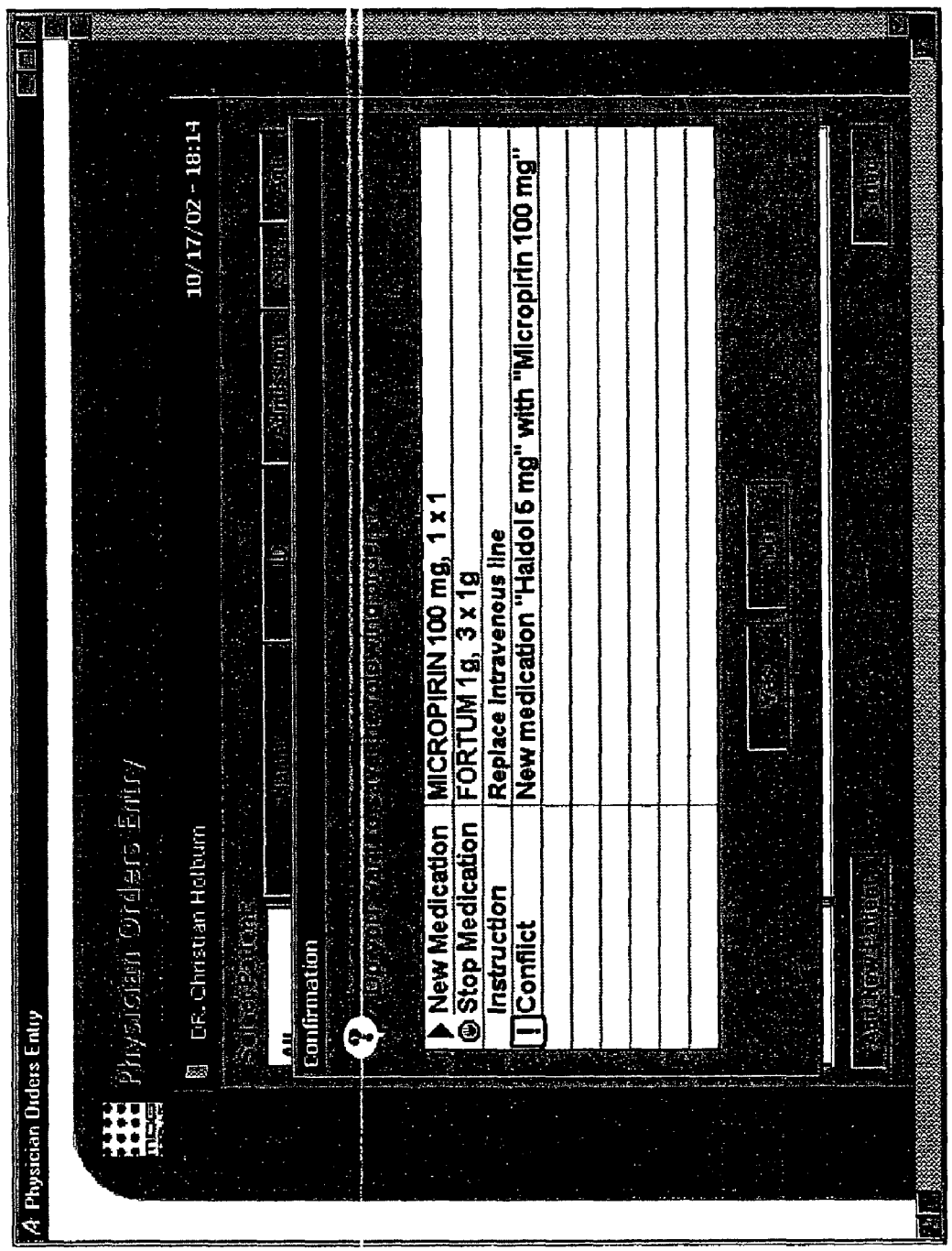
FIG. 14 is an exemplary illustration of a frame of the prescription program in accordance with a preferred embodiment.

A confirmation screen is then displayed to confirm the physician's orders. An exemplary confirmation screen is illustrated in FIG. 14. Preferably, the physician must then confirm the orders that have been entered for the patient by selecting the 'Yes' button, which results in the display of another confirmation screen, thereby further eliminating a point of error. The physician is then asked to input his/her identification means, which causes handheld POE computer 60 to generate the physician's electronic signature, or other electronic identifying means, verifying that the physician is authorized to make such a prescription. The physician may then continue with rounds, visiting the next patient and repeating the process as necessary. Once the physician's rounds have been completed, the physician preferably attaches handheld POE computer 60 to input 24 (i.e., a docking station) coupled to work station 70. Work station 70 transmits the information input by the physician to server 20. Once the information is transmitted to server 20, all information is preferably deleted from handheld POE computer 60, which protects the information from being accessed by unauthorized individuals who may, without authorization, access POE computer 60. When POE computer 60 is to be used by a physician, information for each patient in the ward is preferably transmitted by POE computer 60.

In an alternative embodiment, and in accordance with governing law, any new prescription information that is transmitted to the pharmacy computer for clinical screening by an authorized pharmacist. The pharmacist reviews the medications prescribed and the patient information, and verifies that no negative implications would result therefrom. Also, the pharmacist confirms that the dosage of prescribed medicine is valid for the patient receiving it. If the pharmacist does not confirm the prescription, the prescribing physician is contacted. This is preferably accomplished by interfacing with pre-existing pharmacy software on the pharmacy computer. Alternatively, this is done by providing the pharmacy with a work station that accesses the workflow program, or by providing the pharmacy computer with access to the workflow program.

In a wireless setting, the physician orders may be transmitted by the physician to the pharmacy computer and the workflow program. In a alternative embodiment, the prescribing program may be accessed from a remote location, such as the Internet and the like.

When the new orders arrive at workstation 70 the attendant is alerted by the workflow program to verify the new orders. Each attendant verifies his/her patients' new instructions by reading them and deploying them to the rounds times according to the frequency ordered by the physician. The workflow program in response to the deployment of all the new orders, along with the already existing orders, creates a scheduler for the ward for the day, and for the following days. The scheduler displays all orders to be performed according to the time at which they are to be performed. The orders may also be displayed by patient and his/her orders are spread over the prescheduled time(s) for administration. It is this scheduler which alerts the attendant to start a medication round or vital sign collection round, or administer a specific medication to one patient, to be disclosed below.

Preparing Dosages

At the prescheduled time for dispensing medications, or when the dispensing of medication is otherwise needed, work station 70 preferably alerts a healthcare attendant using display 77. In a preferred operation, work station 70 transmits to cabinet 30 the list of patients to receive medication at that time, and when required, it identifies each patient, the medication, and the dosage for that patient. The alert continues until the authorized attendant selects the task for which the alert was sent.

Figure 15:
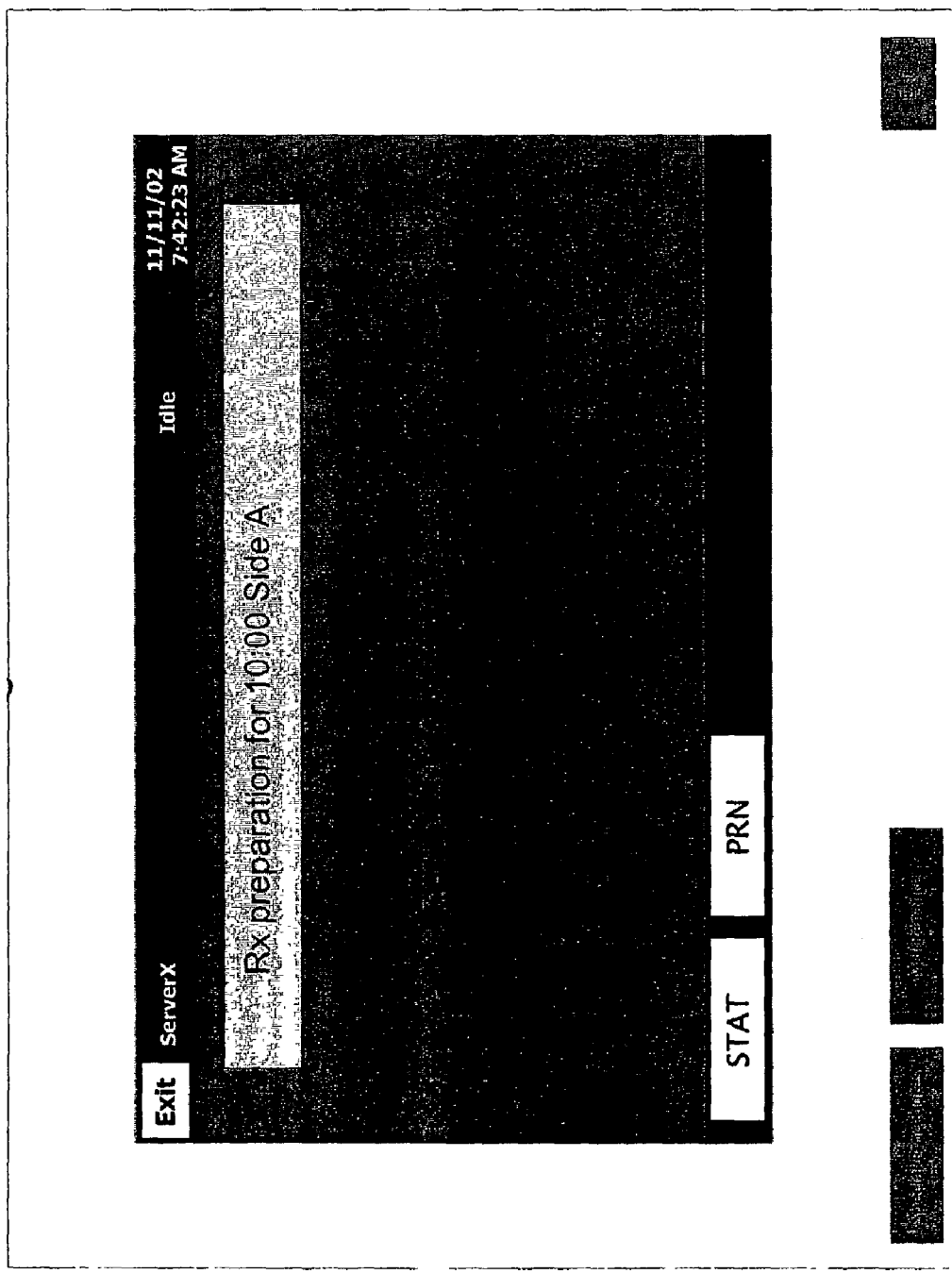
FIG. 15 is an exemplary illustration of a medication preparation frame of the cabinet program in accordance with a preferred embodiment.

Once medicine cabinet 30 has received the information from the workflow program, touch screen 34 displays a medication preparation screen, such as that which is exemplified in FIG. 15. Preferably, the healthcare attendant assigned to administer medications to the patients in the ward associated with medicine cabinet 30 must identify himself or herself in order to access medicine cabinet 30 using an identification means, such as a password code, a personal identification means or a biometric identification means. Preferably, this information is input using cabinet touch screen 34. When the correct identification information has been entered, medicine cabinet 30 may be accessed by the authorized attendant.

As disclosed hereinabove, an authorized healthcare attendant administers scheduled medications to the plurality of patients in the ward using mobile cart 50. Accordingly, it is preferable that cart 50 be coupled to, and in communication with, cabinet 30 through communication link 37 of cabinet 30 and communication link 55 of cart 50.

Once server 20 has verified the attendant's authorization information, the cabinet program initializes the instructions for the attendant to fill cart 50 for administration of medications to the respective ward patients. Since a ward may have more than one medication cart 50 available for administering medications, the authorized healthcare attendant is asked to select and identify the medication cart that is to be filled.

Figure 16:
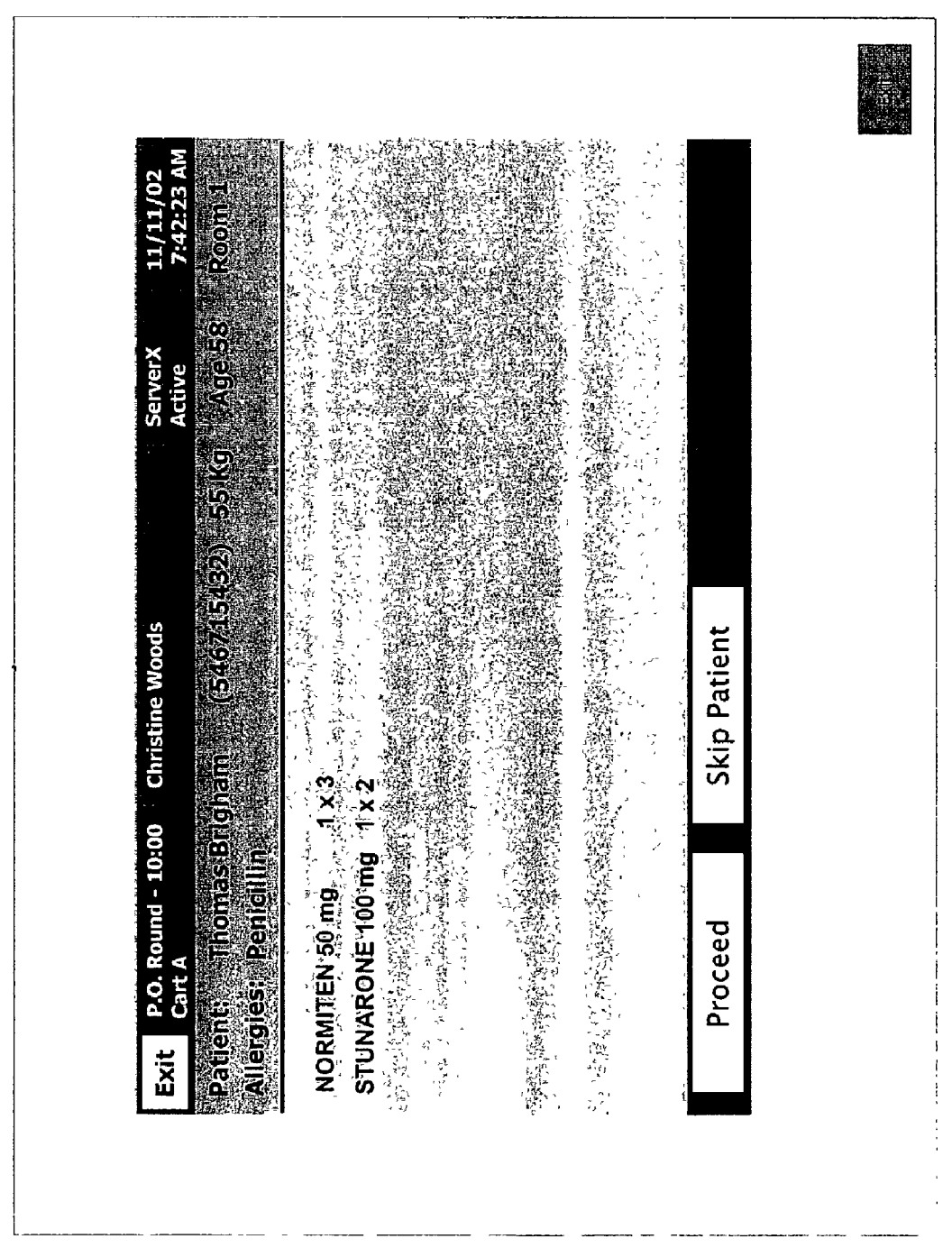
Figure 17:
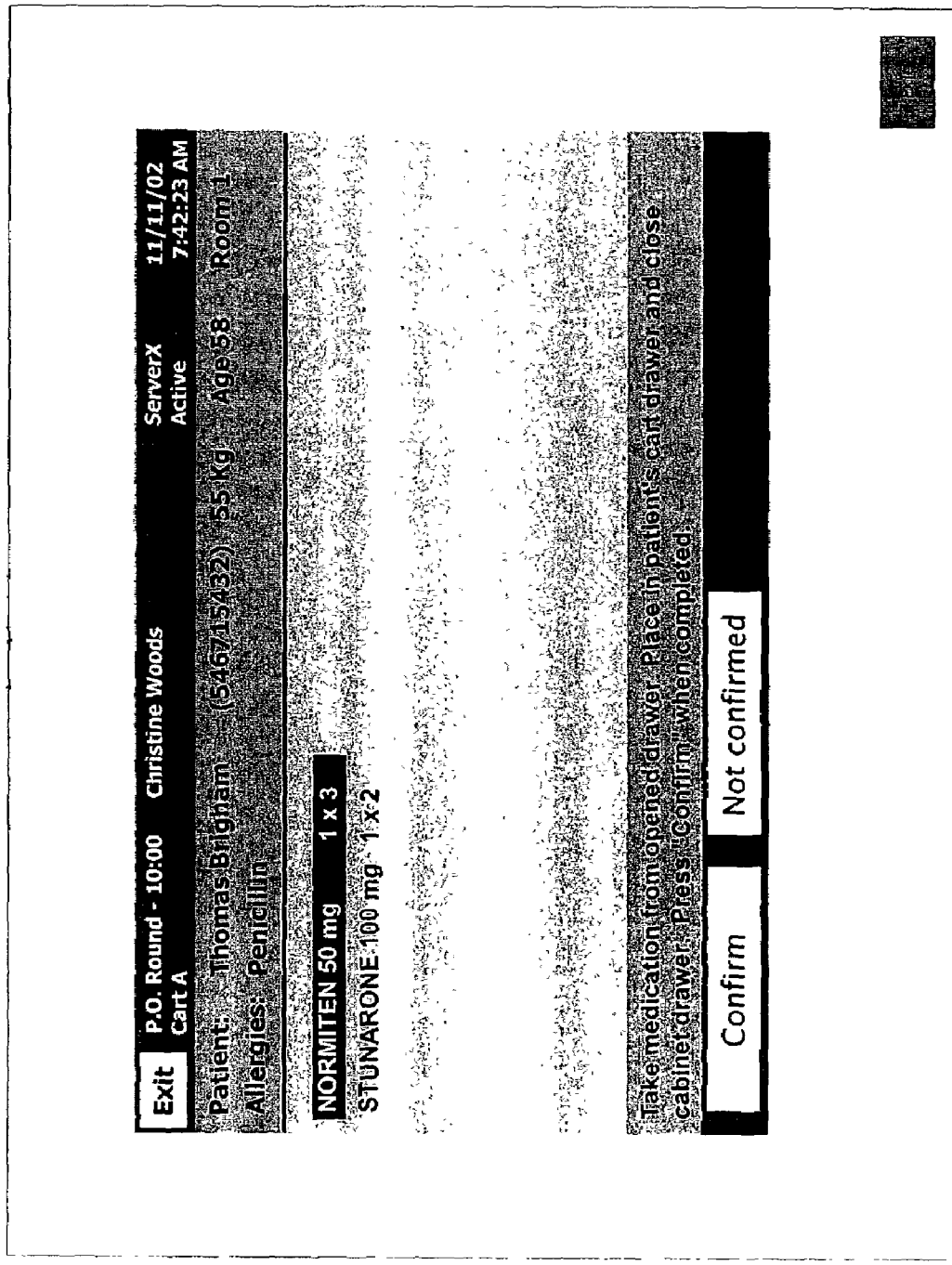
FIG. 17 is an exemplary frame of the cabinet program which illustrates instructions for dispensing medications from the cabinet.

Once the attendant has selected the cart to be used during the rounds, a patient is chosen from the list of patients in the ward that are to receive medication and the chosen patient's name, ID and medications to be administered is displayed on display 34, as exemplified in FIG. 16. To ensure that in each case the correct medication is administered to the appropriate patient in the right amount, the cabinet program displays instructions that the healthcare attendant is to follow on screen 34 of cabinet 30 in filling cart 50. Cabinet processor 38 controls the healthcare attendant's access to the medication in the respective medication specific drawers 31 of cabinet 30 and access to drawers 51 of cart 50 via the cabinet program. Accordingly, once the patient has been selected, the medication to be dispensed is then selected and the healthcare attendant instructed on dispensing the medication into cart 50. An exemplary illustration of the selection of the medication and the instructions related thereto is shown in FIG. 17.

Processor 38 forwards the selected patient to cart processor 52, which assigns a specific drawer 51 of medication cart 50 for the selected patient and displays the name of the patient assigned to the assigned drawer 51 on display 510 of the selected drawer 51. The assignment of the drawer by cart processor 52 changes the identification of cart 50 from an unidentified cart to a dispensing cart comprising a plurality of patient specific drawers.

After patient specific drawer 51 has been assigned by cart processor 52, processor 38 forwards an open drawer signal simultaneously to both a cabinet medication specific drawer 31 and cart processor 52. The medication specific drawer 31, which has the selected medication stored therein, receives the open signal and unlocks and springs forward the medication specific drawer 31, all other drawers of cabinet 30 preferably remain locked and closed. Simultaneous to the opening of medication specific drawer 31 of cabinet 30, cart processor 52 receives the open signal from cabinet processor 38, sends an open drawer signal to the patient specific drawer 51 assigned to the selected patient, causing patient specific drawer 51 to unlock and spring forward, all other drawers of cart 50 remaining locked and in a closed position.

In at least one embodiment, the authorized healthcare attendant, having opened medication specific drawer 31 and patient specific drawer 51 open, follows the directions displayed on display 34 of cabinet 30 to fill open patient specific drawer 51. For example, in practice, the attendant takes the appropriate dose of a medication from an open medication specific drawer 31 of cabinet 30 and preferably scans the bar code label of the medication. This verifies that the correct medication has been retrieved from cabinet 30. Alternatively, and preferably in addition, the attendant verifies the medication visually. When the correct medication has been retrieved, the medicine is placed in open patient specific drawer 51 of cart 50. Following the instructions displayed, the attendant then closes medication specific drawer 31 of cabinet 30.

Processor 38 of cabinet 30 detects the closing of medication specific drawer 31. If there is another medication that is to be dispensed to the selected patient, cabinet processor 38 identifies the next medication for the selected patient, and forwards another open drawer signal to the medication specific drawer that has the selected medication stored therein. Again, a medication specific drawer of cabinet 30 receives the signal from the cabinet processor 38, unlocking and causing the drawer to spring forward. The attendant repeats the steps disclosed above for removing the medication from cabinet 30 and places the appropriate amount of the identified medication in already open patient specific drawer 51 of cart 50, as disclosed above.

The foregoing process continues until all specified medication for the respective patient has been removed from the cabinet 30 and placed into the patient's patient specific drawer 51. It should be noted that the medication selected by cabinet processor 38 may be stored in a patient specific drawer of cabinet 30. Accordingly, cabinet processor 38 forwards an open signal to the patient specific drawer located in cabinet 30 assigned to the selected patient, which is then opened. As disclosed above, the cabinet patient specific drawer is used to store medications that are not generally stored in the medication specific drawers of cabinet 30. Special medications, stored in the special compartments of cabinet 30, are also dispensed to the patient specific drawers of cart 50 in the manner disclosed above. If narcotics are to be administered, the attendant is preferably required to re-enter his/her identification means. It should be noted that requirements for administering narcotics are dependant on the medical institution's policies or governmental requirements. For those medications, if any, that cannot fit within the open patient specific drawer 51, the attendant is instructed to bar code the medications and place the medication into cart drawer 52. These medications are preferably labeled with the patient ID barcode for positive identification during administration of the medication.

Once all of the medications for the selected patient have been placed in open cart drawer 51, 52, cabinet processor 38 then instructs the attendant to close the open patient specific drawer 51. The system then repeats the foregoing operations with respect to all of the other patients list, to receive medications at that time each patient being assigned a separate drawer in cart 50 and his/her respective medications placed therein. Each patient specific drawer displays the name of the respective patient assigned to the drawer on the display of the respective drawer as disclosed above.

At any time during this process, if the prescribed medication is not available in cabinet 30, cabinet 30 guides the authorized attendant via its display to order the medication from the central pharmacy; at the same time, work station 70 issues an order form to the central pharmacy, or otherwise orders the appropriate medication through its communication with the central pharmacy.

In a centralized system comprising a central pharmacy, medicine cabinet 30 is utilized to store unit dose medications for each patient, the unit dose for a 24 hours period. Patient specific drawers 31 of cabinet 30 are assigned to each patient wherein the unit dose medications for each patient are stored and accessed to fill cart 50 each round. The patient specific drawers are then replenished at the end of the 24 hour period with the unit dose medications for the next 24 hour period. If there are changes to the orders or new PRN or stat medication, the requested medication is dispensed from the medication specific drawers 31 of cabinet 30.

Although it is preferable that cart 50 is filled before each round and emptied after each round, cart 50 is alternatively filled with 24 hours of patient medications and used for each round within the 24 hours. Cart processor 52 assigns the cart patient specific drawer 51 to each patient in the respective ward once every 24 hours. Patients that are admitted to the ward during the 24 hour period are also assigned to a patient specific drawer by cart processor 52.

Alternatively, cart processor 50 assigns a patient specific drawer to each patient, wherein the assigned drawer remains assigned to the patient until the patient is transferred from the ward associated with the cart or discharged from the institution. Accordingly, after the all medications for the 24 hour period have been administered to the patients assigned to cart 50, containers including each patient's medications for the next 24 hours is used to refill each patient specific drawer. The manner upon which each drawer is filled is similar to the method disclosed above regarding the filling of the cart from medications stored in the medicine cabinet. Display 54 of cart 50, displays, for example, the patient's name, allergies, medications, dosages and instructions on filling the patient's drawer.

Delivery of Medications to the Patients

After cart 50 has been filled for each patient receiving medication, the authorized healthcare attendant wheels cart 50 to the patients in the ward for administration of their respective medications. The attendant preferably delivers the medications to the patients in the following manner for each:

When the attendant arrives with cart 50 at the patient's bedside, the attendant preferably uses bar code reader 57 to scan the patient's wristband. Cart processor 52 detects the patient code input by bar code reader 57, compares the received code to the patient codes stored therein, associates the code with a patient, and causes the patient's specific drawer 51 to be unlocked and pushed forward, wherein the other drawers of cart 50 remain locked and in the closed position. The patient's name is also displayed on screen 54 together with the list of medications contained within the respective patient specific drawer 51, the total number of medications in drawer 51, and the list of vital signs to be obtained by the attendant, for example, other patient specific information, e.g., age, weight, allergies, etc. If a prescribed medication was not been available from medicine cabinet 30, and therefore, had been ordered directly from, the central pharmacy as described above, cart display 54 would include a reminder of this fact to the attendant.

The attendant then counts the total number of medications in the open patient specific drawer 51, and matches the total number counted with the total number of medications shown on display 54. Assuming a match occurs in all respects, the attendant then administers the medication to the patient. Alternatively, the attendant may scan each medication in the patient drawers to verify that the patient is receiving the correct medication. For those medications taken from the common drawer 52, the medications must be scanned for verification.

In an alternative embodiment, cart display 54 displays a list of patients that are to receive medications during the current round. When the attendant arrives at a patient's bedside, the attendant would verify the identification of the patient and select the patient's name from the list of patients displayed on display 54. Once the patient is selected, cart processor 52 operates in the manner set forth above in the preferred embodiment.

During the administration of the medications, the attendant is instructed by cart 50. For each medication to be administered, cart 50 preferably provides step by step instructions. When an IV is administered, the attendant is preferably instructed to check and confirm the flow rate. The attendant is also instructed on which hand or arm the IV or injection should be used, depending on the previous place of administration. Preferably, each time a medication is taken by the patient, the attendant is required by cart 50 to confirm and log this event. If a medication is not taken by a patient, cart 50 preferably requires the attendant to log the reason the medication was not administered. This is also required of the attendant if during the round a patient is not in his/her bed. In this case, the attendant would log that the patient was skipped and the reason therefor. As disclosed above, the logging of these events are transmitted to server 20.

If certain vital signs are to be taken of the patient (e.g., temperature, blood pressure, pulse rate, etc.), as instructed via cart display screen 54, the attendant attends to the gathering of this information and inputs the information via cart connector 58 or manually via keyboard 56. The gathering of this information is also logged and stored in cart 50 until cart 50 is coupled to cabinet 30 for transmitting said information to server 20.

For those cases where the medication administration is conditioned by certain data (i.e., vital sign result or lab result), then the attendant is instructed to check the condition and enter the value for confirmation. If the value allows for the administration of the medication, the attendant will be advised to do so.

Replenishing the Medicine Cabinet

As disclosed above, the workflow program maintains the inventory of medicine cabinet 30 associated therewith. Accordingly, whenever the workflow program detects a "low level" of medication in one of drawers 31, this fact is displayed for the responsible healthcare attendant on display 74 and automatically ordered from the pharmacy via forms, or via a communication channel between the pharmacy computer and the workflow program. Alternatively, the workflow program may request the authorized attendant to reorder the identified medication from the pharmacy.

Work station 70 may be requested at any time to authorize a replenishment from the central pharmacy. If the ordering is done with forms (i.e., without direct communication), the workflow program is preferably supplied with a list of medications received from the pharmacy, including the exact amount of every new medication. The workflow program updates the inventory and transmits this information to medicine cabinet 30. For each such medication, the cabinet program instructs the attendant to perform the following operations:

The attendant opens the packaging of the medication, counts the units, records the count and places the medication in the open drawer. At this time, the attendant again must match the name on the package with the name on the front of the open drawer. For further safety, the attendant may be required to scan the bar code on the medication packaging using cabinet bar code reader 131 to match it with the name of the medication displayed on cabinet screen 34.

The attendant then closes the medication specific drawer. When the closed drawer is sensed by medicine cabinet 30, cabinet processor 38 repeats the foregoing cycle for all the remaining medications on the list for replenishment until all medications are replenished. If during such a replenishing operation the attendant notes that one of the drawers is full, the attendant may press a "full" button on cabinet keyboard 33 (or on display 34, if a touch screen is used), whereupon cabinet processor 33 will open an empty drawer, print a label with the name of the medication, and instruct the attendant to place the label on the new open drawer. Thus, a second medication specific drawer is created for the patient.

It should be noted that a cabinet patient specific drawer is filled and replenished in the same manner as disclosed hereinabove. When cabinet processor 38 determines that a patient specific drawer should be utilized for the received medication, a cabinet drawer assigned to the patient associated with the received medication is opened and the medication placed therein. If no cabinet drawer has been assigned to the patient, processor 38 opens an empty drawer not currently in use, and displays the patient's name on the cabinet drawer LCD display. The attendant is the instructed to place the received medication in the patient specific drawer.

Once all of the medications have been placed in their respective medication or patient specific drawers, the workflow program compares the count values and information regarding each medication as input by the attendant to the count and information received by the pharmacy and identifies any discrepancies.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A medication dispensing system, comprising:

a medicine cabinet having a plurality of drawers each drawer containing supplies of different kinds of medications or other medical supplies to be accessed by a healthcare attendant for preparing individual medication dosages and medical supplies for named patients;

and at least one medicine cart, separate from said medicine cabinet, said cart having a plurality of cart drawers, each drawer adapted to contain one or more medication dosages and medical supplies prescribed for an individual patient;

said medicine cabinet including a cabinet processor having a memory for storing the names of patients and their prescribed medication dosages and medical supplies to be dispensed to said patient; and said cart further comprising a display on each cart drawer for displaying each patient's name corresponding to the medication dosages and medical supplies placed in said drawer, and a communication link with said medicine cabinet through which said cabinet processor communicates to said cart, each said patient's name, medication dosages and medical supplies to be dispensed to said patient.

2. The system according to claim 1, wherein said drawers in the medicine cabinet are normally looked but which are selectively unlocked by said cabinet processor when containing a medical supply to be included in a prescribed medication dosage or medical supply for a named patient.

3. The system according to claim 1, wherein said medical cart further comprises a reader for reading said patient's name to enable matching the read name with a name communicated by said medicine cart of a patient to receive a prescribed medication dosage or medical supply.

4. The system according to claim 3, wherein said reader is a bar code reader to read a bar code carried by the respective patient.

5. The system according to claim 4, wherein at least one of the cabinet drawers includes a refrigeration means for storing medications that require refrigeration.

6. The system according to claim 5, wherein said refrigerated medication is bar coded with a patient ID for the patient for whom the medication has been prescribed.

7. The system according to claim 1, wherein said cabinet processor further stores in its memory a running inventory of each medication supply in each cabinet drawer including all quantities supplied less all dosages removed.

8. The system according to claim 1, wherein the system further comprises a central processor having a memory for storing said patient name and the respective medication dosages prescribed for said patients; and a communication link with said medicine cabinet through which said central processor communicates to said cabinet processor the patient names and their respective presented medication dosages and medical supplies.

9. The system according to claim 8, wherein one of said processors stores in its memory running inventories of the medications and supplies in said cabinet drawers including all quantities introduced into the respective drawer less all dosages removed therefrom.

10. The system according to claim 8, wherein said cart includes an input device for inputting data regarding vital signs of a respective patient, and said communication link of the cart with said cabinet processor communicates said vital signs data to said central processor via said cabinet processor and its communication link wit said central processor.

11. The system according to claim 8, wherein the system further comprises a plurality of portable computer units for use by physicians and/or pharmacists; each of said portable computer units comprising an input device for inputting data regarding a prescribed medication dosage or medical supply for a named patient, a storage device for storing an electronic signature of said user, and a communication link for communicating to said central processor said inputted data and said electronic signature.

* * * * *